US011319382B1

(12) United States Patent
Azhar et al.

(10) Patent No.: US 11,319,382 B1
(45) Date of Patent: May 3, 2022

(54) METHODS FOR PRODUCING AND USING IGY ANTIBODIES TARGETING THE MIDDLE EAST RESPIRATORY SYNDROME CORONAVIRUS SPIKE PROTEIN TO TREAT OR PREVENT MERS-COV INFECTION

(71) Applicant: King Abdulaziz University, Jeddah (SA)

(72) Inventors: Esam Ibraheem Azhar, Jeddah (SA); Sherif Ali El-Kafrawy, Jeddah (SA); Aymn Talat Abbas, Jeddah (SA); Ashraf Abdu Tabil, Jeddah (SA)

(73) Assignee: KING ABDULAZIZ UNIVERSITY, Jeddah (SA)

(*) Notice: Subject to any disclaimer, the term of this patent is extended or adjusted under 35 U.S.C. 154(b) by 0 days.

(21) Appl. No.: 17/360,489

(22) Filed: Jun. 28, 2021

(51) Int. Cl.
*C07K 16/42* (2006.01)
*C07K 14/165* (2006.01)
*A61K 39/00* (2006.01)

(52) U.S. Cl.
CPC ........ *C07K 16/4216* (2013.01); *C07K 14/165* (2013.01); *A61K 2039/505* (2013.01); *A61K 2039/545* (2013.01); *C07K 2317/10* (2013.01); *C07K 2317/23* (2013.01); *C07K 2317/76* (2013.01)

(58) Field of Classification Search
CPC .............. C07K 16/4216; C07K 14/165; C07K 2317/10; C07K 2317/23; C07K 2317/76; A61K 2039/505; A61K 2039/545
See application file for complete search history.

(56) References Cited

U.S. PATENT DOCUMENTS

| 10,428,138 | B2 | 10/2019 | Tsukamoto | |
|---|---|---|---|---|
| 11,131,672 | B1 * | 9/2021 | Abdelhadi | ............. C07K 16/10 |
| 2013/0295109 | A1 | 11/2013 | Scammell | |
| 2020/0325182 | A1 | 10/2020 | Keller et al. | |

FOREIGN PATENT DOCUMENTS

| CN | 103961704 A | 8/2014 |
|---|---|---|
| CN | 104117062 A | 10/2014 |
| CN | 104739719 A | 7/2015 |
| EP | 2 957 570 A1 | 12/2015 |
| JP | 2017006008 A * | 1/2017 |
| MX | 2015004554 A | 8/2015 |
| WO | 2011/155705 A2 | 12/2011 |
| WO | 2012/071346 A1 | 5/2012 |
| WO | 2012/136534 A2 | 10/2012 |
| WO | 2013/009843 A1 | 1/2013 |
| WO | 2013/027356 A1 | 2/2013 |
| WO | 2013/045469 A1 | 4/2013 |
| WO | 2014/011853 A2 | 1/2014 |
| WO | 2016/166246 A1 | 10/2016 |
| WO | 2016/191389 A2 | 12/2016 |
| WO | 2017/065626 A1 | 4/2017 |
| WO | 2018/026604 A1 | 2/2018 |

OTHER PUBLICATIONS

Sivapalasingam S, Saviolakis GA, Kulcsar K, Nakamura A, Conrad T, Hassanein M, Sumner G, Elango C, et al. Human Monoclonal Antibody Cocktail for the Treatment or Prophylaxis of Middle Eastern Respiratory Syndrome Coronavirus (MERS-CoV). J Infect Dis. Jan. 28, 2021:jiab036. Epub ahead of print. (Year: 2021).*
MERS-CoV Antigen Protein. https://www.sinobiological.com/research/virus/mers-cov-proteins-reagent. Sino Biological, Accessed Oct. 7, 2021. Available by Apr. 19, 2015. (Year: 2015).*
MERS-CoV Spike/S1 Protein (S1 Subunit, aa1-725, His Tag). Cat. #: 40069-V08H. Sino Biological, Accessed Oct. 7, 2021. Available by Apr. 19, 2015. (Year: 2015).*
El-Kafrawy SA, Abbas AT, Sohrab SS, Tabll AA, Hassan AM, Iwata-Yoshikawa N, et. al. Immunotherapeutic Efficacy of IgY Antibodies Targeting the Full-Length Spike Protein in an Animal Model of Middle East Respiratory Syndrome Coronavirus Infection. Pharmaceuticals (Basel). May 26, 2021;14(6):511. (Year: 2021).*
Van Boheemen S, et. al. S protein [Human betacoronavirus 2c EMC/2012]. GenBank: AFS88936.1, Dep. Dec. 4, 2012. (Year: 2012).*
Lu Y, Wang Y, Zhang Z, Huang J, Yao M, Huang G, Ge Y, Zhang P, Huang H, Wang Y, Li H, Wang W. Generation of Chicken IgY against SARS-COV-2 Spike Protein and Epitope Mapping. J Immunol Res. Oct. 17, 2020;2020:9465398. (Year: 2020).*
Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

(Continued)

*Primary Examiner* — Rachel B Gill
(74) *Attorney, Agent, or Firm* — WC&F IP

(57) ABSTRACT

Chicken egg yolk antibodies (IgY Abs) specific to the Middle Eastern Respiratory Syndrome coronavirus spike (MERS-CoV S) protein demonstrate efficacy against MERS-CoV infection. The S-specific IgY Abs (anti-S IgY) are produced by injecting chickens with purified a recombinant MERS-CoV S protein, S1 subunit, or an S1 fragment. The purified anti-S IgY specifically bind to the MERS-CoV S protein and inhibit infection. In vitro neutralization of the IgY Abs against MERS-CoV was achieved in cell lines and in a human-transgenic mouse model treated with a pharmaceutical composition comprising the anti-S IgY. Viral antigen-positive cells in treated mice were reduced, compared to the adjuvant-only controls. Moreover, lung cells of anti-S IgY-treated mice showed significantly reduced inflammation, compared to the controls. Efficient neutralization of MERS-CoV infection is demonstrated both in vitro and in vivo using the anti-S IgY Abs.

14 Claims, 18 Drawing Sheets

Specification includes a Sequence Listing.

(56) References Cited

OTHER PUBLICATIONS

Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*

Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*

Sela-Culang I, Kunik V, Ofran Y. The structural basis of antibody-antigen recognition. Front Immunol. Oct. 8, 2013;4:302. (Year: 2013).*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year : 2015).*

Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Somasundaram R, Choraria A, Antonysamy M. An approach towards development of monoclonal IgY antibodies against SARS CoV-2 spike protein (S) using phage display method: A review. Int Immunopharmacol. Aug. 2020;85:106654. Epub Jun. 3, 2020. (Year: 2020).*

Hashem AM, Al-Amri SS, Al-Subhi TL, Siddiq LA, Hassan AM, Alawi MM, Alhabbab RY, Hindawi SI, Mohammed OB, Amor NS, Alagaili AN, Mirza AA, Azhar EI. Development and validation of different indirect ELISAs for MERS-CoV serological testing. J Immunol Methods. Mar. 2019;466:41-46. (Year: 2019).*

Abbas et al: "IgY antibodies for the immunoprophylaxis and therapy of respiratory infections", Human Vaccines & Immunotherapeutics, vol. 15, No. 1, pp. 264-275, 2019.

Modjarrad: "Research and Development Activities for Middle East Respiratory Syndrome: The Current Landscape", WHO, Oct. 15, 2020.

Zhao et al: "Passive Immunotherapy with Dromedary Immune Serum in an Experimental Animal Model for Middle East Respiratory Syndrome Coronavirus Infection", Journal of Virology, vol. 89, No. 11, pp. 6117-6120, Jun. 2015.

Abbas et al: "Anti-S1 MERS-COV IgY Specific Antibodies Decreases Lung Inflammation and Viral Antigen Positive Cells in the Human Transgenic Mouse Model", Vaccines, vol. 8, No. 634, Nov. 1, 2020.

Lu et al: "Generation of Chicken IgY against SARS-COV-2 Spike Protein and Epitope Mapping", Journal of Immunology Research, Oct. 17, 2020.

Somasundaram et al: "An approach towards development of monoclonal IgY antibodies against SARS COV-2 Spike protein (S) using phage display method: A review", International Immunopharmacology, vol. 85, 2020.

Suarez et al: "Lack of Susceptibility to SARS-CoV-2 and MERS-CoV in Poultry", Emerging Infectious Disease, vol. 26, No. 12, pp. 3074-3076, Dec. 2020.

Tsukamoto et al: "Protection against Infectious Bronchitis Virus, a Corona Virus Infection, using Ostrich Antibodies", Health, vol. 20, pp. 1294-1308, Oct. 12, 2018.

Wei et al: "A chicken IgY can efficiently inhibit the entry and replication of SAR-CoV-2 by targeting the ACE2 binding domain in vitro", China, 2021.

\* cited by examiner

FIGURE 2

Kinetics of MERS-CoV S-IgY Abs in Serum and Eggs

- Eggs
- Serum
- Adjuvant Control

[Bar graph: Virus titer (Log$_{10}$ TCID$_{50}$/g) vs Days after inoculation (1, 3, 5)]

○ MERS-CoV S IgY
■ Isotype cont. (Adjuvant)

7B

[Line graph: Percent change from initial weight (%) vs Days after inoculation (0-8)]

─○─ MERS-S IgY  ─■─ Isotype cont.

METHODS FOR PRODUCING AND USING IGY ANTIBODIES TARGETING THE MIDDLE EAST RESPIRATORY SYNDROME CORONAVIRUS SPIKE PROTEIN TO TREAT OR PREVENT MERS-COV INFECTION

BACKGROUND OF THE INVENTION

Field of the Invention

The invention generally relates methods of producing a therapeutic composition of antibodies to treat or inhibit Middle East Respiratory Syndrome coronavirus (MERS-CoV) infection. The invention further relates to methods of producing and using chicken egg yolk antibodies (IgY) to treat or inhibit infectious disease, particularly MERS-CoV.

Background

Respiratory infections affect millions of people worldwide and pose risks to many, especially children and the elder. Middle East respiratory syndrome coronavirus (MERS-CoV) is an emerging zoonotic virus causing severe and often fatal respiratory illness in humans. MERS-CoV was first detected in 2012. Since then, documented infections in humans have steadily increased, with 2,566 cases as of December 2020 and an estimated 35% fatality rate. The virus can be transmitted from camel to camel, and dromedary camels demonstrate high seropositivity to MERS-CoV. Transmission from camel to human also occurs, and several risk factors, such as direct contact with infected dromedary camels, have been identified. Importantly, MERS-CoV remains endemic in the Middle East. However, it may have pandemic potential, as it has been introduced into other countries via air travel, including an outbreak in South Korea involving more than 100 cases.

Thus far, the most promising treatment is the passive administration of anti-MERS-CoV neutralizing antibodies. Several research groups have developed and produced anti-MERS patient-derived or humanized monoclonal neutralizing antibodies in vitro that can protect MERS-CoV-infected mice (Zhao, Li et al. 2014, Corti, Zhao et al. 2015, Li, Wan et al. 2015, Widjaja, Wang et al. 2019). These antibodies react with a single epitope on the MERS-CoV spike (S) protein, which is prone to mutations, thus raising the possibility of antibody escape (Corti, Zhao et al. 2015, Sabir, Lam et al. 2016). A previous study of passive immunotherapy found that camel serum significantly reduced virus loads and accelerated virus clearance from the lungs of MERS-CoV-infected mice (Zhao, Perera et al. 2015). In another study, equine immunoglobulin-derived F(ab')2 fragments administered to MERS-CoV-infected mice yielded similar results (Zhao, Wang et al. 2017).

Immunoglobulin Y (IgY) is the primary antibody in oviparous animals. It is the only antibody transferred to the egg yolk, from which it can be easily isolated using precipitation techniques. In recent years, IgYs have drawn considerable attention as potential alternatives for passive immunization (Yi, Qin et al. 2018). IgYs are safer than antibodies from other species such as IgGs because they do not bind to human Fc receptors or fix mammalian complement components; hence, they do not trigger potentially dangerous immune responses. Chickens can produce eggs with IgY antibodies on a large scale using non-invasive and humane methods, which may offer new, economically feasible, and efficient immunotherapy options (Sharma 1999, Pauly, Dorner et al. 2009, Xu, Li et al. 2011, Gadde, Rathinam et al. 2015, Li, Wang et al. 2015). Furthermore, IgY has greater binding avidity to target antigens than mammalian IgG (Ikemori, Peralta et al. 1993), and it can be produced against conserved mammalian proteins more easily and more successfully than IgG can be produced in other mammals due to the evolutionary distance between mammals and birds. IgYs also induce an efficient immune response in low quantities (Li, Wang et al. 2015).

Specific IgY antibodies have proven highly effective for the prevention and treatment of respiratory viral and bacterial diseases such as influenza A (Nguyen, Tumpey et al. 2010, Tsukamoto, Hiroi et al. 2011, Wallach, Webby et al. 2011, Yang, Wen et al. 2014), influenza B (Wen, Zhao et al. 2012), SARS coronavirus (Fu, Huang et al. 2006), bovine respiratory syncytial virus (Ferella, D. Bellido et al. 2012), and *Mycobacterium tuberculosis* (TB) infection (Sudjarwo, Eraiko et al. 2017). IgY technology has been successfully applied in clinical trials against *Pseudomonas aeruginosa* lung infection (Kollberg, Carlander et al. 2003). In 2008, the European Medicines Agency granted an orphan drug designation to IgY for the treatment of cystic fibrosis. Another recent study demonstrated that IgY antibodies transiently decrease *P. aeruginosa* colonization in the airways of mechanically ventilated piglets (Otterbeck, Hanslin et al. 2019). Moreover, specific IgY antibodies could protect mice against pneumonia caused by *Acinetobacter baumannii* (Jahangiri, Owlia et al. 2018).

The MERS-CoV S protein engages with the viral cellular receptor dipeptidyl peptidase 4 (DPP4) to mediate viral attachment to host cells and subsequent fusion of the virus with the cell membrane (Lu, Hu et al. 2013, Raj, Mou et al. 2013, Li 2015). The S protein plays a key role in counteracting coronavirus infection, as shown in studies on human-neutralizing antibodies from rare memory B cells in individuals infected with SARS-CoV (Traggiai, Becker et al. 2004) or MERS-CoV (Corti, Zhao et al. 2015). In such studies, antibodies targeting the S protein of SARS-CoV effectively inhibited virus entry into host cells. More recently, it has been found that SARS-CoV S elicits polyclonal antibodies that vigorously neutralized SARS-CoV-2 S-mediated entry into cells, thus encouraging the use of this molecular target for vaccination and immunotherapies (Walls, Park et al. 2020). Thus far, the most promising treatment is the passive administration of anti-MERS-CoV neutralizing antibodies. Several research groups have developed and produced anti-MERS patient-derived or humanized monoclonal neutralizing antibodies in vitro that can protect MERS-CoV-infected mice (Zhao, Li et al. 2014, Corti, Zhao et al. 2015, Li, Wan et al. 2015, Widjaja, Wang et al. 2019). These antibodies react with a single epitope on the MERS-CoV spike (S) protein, which is prone to mutations, thus raising the possibility of antibody escape (Corti, Zhao et al. 2015, Sabir, Lam et al. 2016). A previous study of passive immunotherapy found that camel serum significantly reduced virus loads and accelerated virus clearance from the lungs of MERS-CoV-infected mice (Zhao, Perera et al. 2015). In another study, equine immunoglobulin-derived F(ab')2 fragments administered to MERS-CoV-infected mice yielded similar results (Zhao, Wang et al. 2017).

Despite wide interest in combating this dangerous infection, there are no approved treatments for MERS-CoV or vaccines to prevent it in humans, camels or other susceptible animals. Therefore, is still a need for novel antiviral strategies to combat the spread of the virus and provide efficacious treatment of MERS-CoV infection.

SUMMARY OF THE INVENTION

The invention relates to in vitro and in vivo methods and compositions comprising anti-MERS-CoV S1 IgY antibodies to neutralize the MERS-CoV virus. The invention further comprises chicken egg yolk antibodies (IgY Abs) specific to the MERS-CoV spike (S) protein.

In one embodiment, the invention is a method of generating IgY Abs against MERS-CoV spike protein by immunizing hens and isolating the IgY Abs from eggs laid by the hens.

In another embodiment, the MERS-CoV-specific IgY is a treatment for MERS-CoV infection in a subject. In another embodiment, the invention is a method for using IgY Abs to inhibit and/or treat disease in a subject at risk for MERS-CoV infection. In some embodiments, the subject may be a human and/or a camel.

The method of producing immunoglobulin Y (IgY) antibodies against Middle Eastern respiratory syndrome coronavirus (MERS-CoV), comprises the steps of immunizing hens with a spike protein from the MERS-CoV, and isolating the IgY antibodies against the MERS-CoV spike protein from yolks of eggs laid by the immunized hens. In one embodiment, the spike protein of the MER-CoV is used as the immunogen for injection into hens. In some embodiments, a fragment of the spike protein is the immunogen. In another embodiment, the spike protein has the amino acid identity of SEQ ID NO:1.

In one embodiment, the invention is a pharmaceutical composition comprising IgY antibodies against MERS-CoV, wherein the IgY antibodies are produced in eggs laid by hens immunized with a spike protein from the MERS-CoV. In one embodiment, the pharmaceutical composition comprises IgY antibodies against a spike protein having the amino acid sequence identity of SEQ ID NO:1.

In yet another embodiment, the invention is a method of inhibiting or treating a MERS-CoV infection in a subject in need thereof, comprising the steps of isolating IgY antibodies to MERS-CoV, wherein said IgY antibodies to MERS-CoV are generated by immunizing hens with a spike protein from the MERS-CoV; preparing a pharmaceutically acceptable composition comprising the IgY antibodies; and administering a therapeutically effective amount of the composition to the subject.

The route of administration of the pharmaceutical composition is selected from the group consisting of intravenous injection, intravenous infusion, intraperitoneal injection intraperitoneal infusion, intranasal, oral, or any other route deemed feasible by a practitioner. The therapeutically effective amount is in the range of 1 to 1,000 mg/kg. In some embodiments, the therapeutically effective amount is in the range of 5 to 500 mg/kg, 10 to 100 mg/kg, 15 to 50 mg/kg or 15 to 25 mg/kg. In one embodiment, the therapeutically effective amount is 0.5 mg/kg. In yet another embodiment, the therapeutically effective amount is 20 mg/kg. The treatment may be administered to a subject who is a human, a camel, a rodent, a primate, or any other subject susceptible to infection by MERS-CoV.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

In FIG. 1A, the two IgY chains appeared using 10% resolving SDS-PAGE gel. The molecular weight of the heavy chain is 68 kDa, and the molecular weight of the light chain is 27 kDa. FIG. 1B shows identification of IgY by Western blot using anti-chicken IgY (IgG) alkaline phosphatase antibody (whole molecule) produced in rabbits to detect heavy chains and light chains of chickens.

FIG. 2 shows kinetics of chicken serum and egg yolk antibody response to anti-MERS-CoV S IgY after infection with MERS-CoV S recombinant protein, compared with adjuvant-only controls. Each week is represented by a pool of egg yolks of individual chickens from each group (S-immunized and adjuvant-only).

In FIG. 3A, the S protein of MERS-CoV is subjected to SDS-PAGE under reducing conditions. FIG. 3B shows a western blot analysis of the anti-S IgY antibody response.

FIGS. 7A-7E show analyses of mice treated with anti-S IgY antibodies. FIG. 7A shows the virus titer in lungs of MERS-CoV-infected mice treated with anti-S IgY antibodies or with adjuvant only. FIG. 7B shows body weight changes between mice with anti-S IgY antibodies and the adjuvant-only controls after MERS-CoV infection. FIGS. 7C-7F show histopathology of the lungs from human dipeptidyl peptidase 4-transgenic mice on day 8 after infection with MERS-CoV, as follows: (7C) Representative histopathological findings of mice with highest cellular infiltration in the alveoli, identified using hematoxylin and eosin staining. Massive mononuclear cell infiltrations, including macrophages and lymphocytes with regenerated type II pneumocytes, were observed in the control group (right column) but slightly less in the group treated with anti-S IgY (left column). Scale bars: 200 μm (upper row) and 20 μm (lower row). Al, alveoli; Br, bronchi; V, vessel. (7D) Quantification of inflammation areas. Pulmonary lesion areas were determined based on the mean percentage of affected areas in each section of the collected lobes from six animals. Circles indicate averages from three observation lobes in each mouse (p=0.041 by Mann-Whitney test). (7E) Detection of viral antigen in the lung tissues of mice, determined by immunohistochemistry. Antigen-positive cells were observed less frequently in the lungs of the group treated with anti-S-IgY (IgY(S)), compared to the adjuvant-only controls (IgY (adjuvant)). Scale bars: 20 μm. (7F) Numbers of viral-antigen-positive cells in the alveoli from six mice. Circles indicate averages of five observation fields in each mouse (p=0.258 by Mann-Whitney test).

FIG. 8A, the S1 protein of MERS-COV was subjected to SDS-PAGE under reducing conditions. FIG. 8B, Western blot analysis of the anti-S1 IgY antibody response. SDS gels were electrically transferred onto nitrocellulose membranes and probed with IgY from immunized and nonimmunized hens (marker: molecular maker; lane A: S1-immunized IgY; lane B: adjuvant-immunized IgY).

FIG. 12A shows representative images of treated cells. MERS-CoV (MOI 0.01) was incubated with different concentrations of anti-S1 IgY antibodies and added to Vero E6 cells. After virus adsorption, agar medium was added to the Vero E6 cells, and the plaques that formed were stained with crystal violet. FIG. 12B shows quantitation of the inhibition of anti-S1 IgY antibodies with different concentrations. (P<0.005, IgY concentration at 2 mg/mL compared with virus control)

FIGS. 13A and 13B show the effects of treatment of mice with anti-S1 IgY antibodies. FIG. 13A shows a viral titer in the lungs of MERS-CoV mice treated with anti-S1 IgY antibodies and control IgY (adjuvant). FIG. 13B shows body weight changes after MERS-CoV infection between anti-S1 IgY antibodies and IgY of adjuvant control group.

DETAILED DESCRIPTION

Figure 1A:
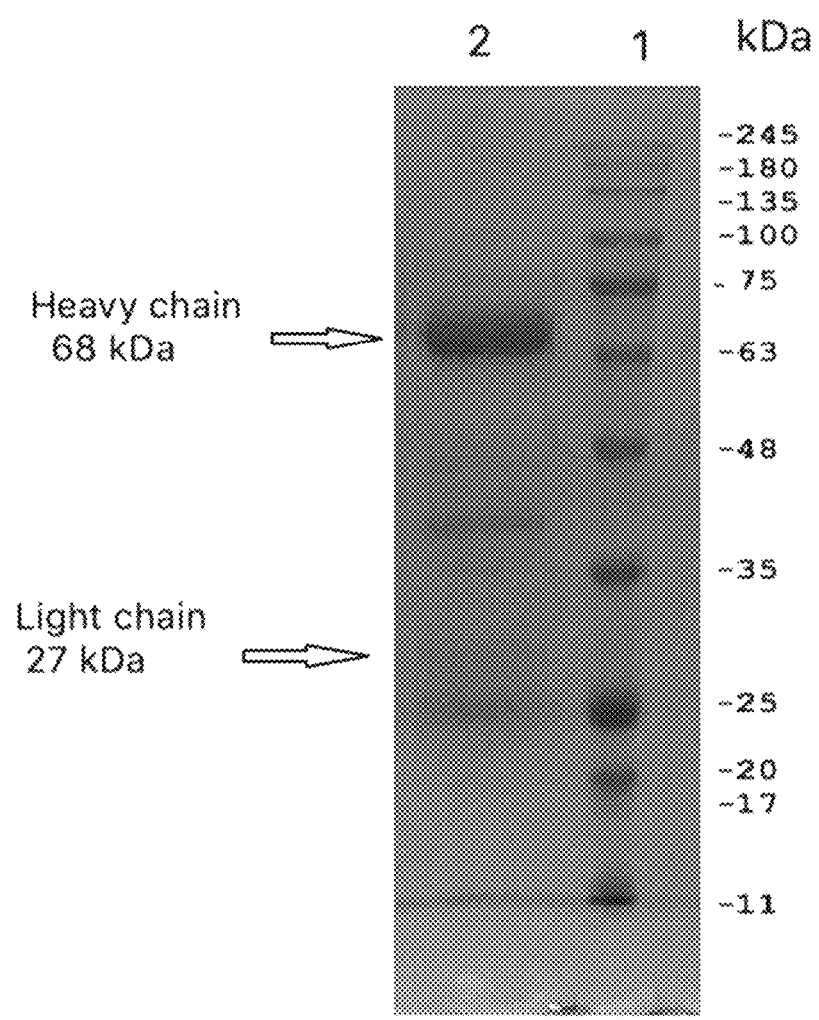
FIGS. 1A and 1B show the SDS-PAGE profile of anti-MERS-CoV S IgY antibodies and a western blot identifying IgY.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

Middle East respiratory syndrome coronavirus (MERS-CoV) causes severe and often fatal acute respiratory illness in humans.

The invention relates to in vitro and in vivo methods and compositions comprising anti-MERS-CoV S1 IgY antibodies to neutralize the MERS-CoV virus. The invention further comprises chicken egg yolk antibodies (IgY Abs) specific to the MERS-CoV spike protein.

In one embodiment, the invention is a method of generating IgY Abs against MERS-CoV spike protein by immunizing hens and isolating the IgY Abs from eggs laid by the hens. The immunogen may comprise a full-length S protein, an S1 protein, or a fragment thereof. In one embodiment, the immunogen is a Met1-Trp1297 fragment of the full-length protein of GenBank Accession number AFS88936.1. The Met1-Trp1297 fragment has the amino acid identity of SEQ ID NO:1.

In another embodiment, the MERS-CoV-specific IgY is a treatment for MERS-CoV infection in a subject. In another embodiment, the invention is a method for using IgY Abs to inhibit and/or treat disease in a subject at risk for MERS-CoV infection.

The method of producing immunoglobulin Y (IgY) antibodies against Middle Eastern respiratory syndrome coronavirus (MERS-CoV), comprises the steps of immunizing hens with a spike protein from the MERS-CoV, and isolating the IgY antibodies against the MERS-CoV spike protein from yolks of eggs laid by the immunized hens. In one embodiment, the S protein of the MER-CoV is used as the immunogen for injection into hens. The amount of immunogen used for immunizing hens is in the range of 10 to 1,000 µg. In one embodiment, the immunogen administered to hens is in the range of 100 to 500 µg. In one embodiment, the amount of immunogen is in the range of 150 to 250 µg.

In one embodiment, the invention is a pharmaceutical composition comprising IgY antibodies against MERS-CoV, wherein the IgY antibodies are produced in eggs laid by hens immunized with a spike protein from the MERS-CoV. In one embodiment, the pharmaceutical composition comprises IgY antibodies against a spike protein having the amino acid sequence identity of SEQ ID NO:1.

In yet another embodiment, the invention is a method of inhibiting or treating a MERS-CoV infection in a subject in need thereof, comprising the steps of isolating IgY antibodies to MERS-CoV, wherein said IgY antibodies to MERS-CoV are generated by immunizing hens with a spike protein from the MERS-CoV; preparing a pharmaceutically acceptable composition comprising the IgY antibodies; and administering a therapeutically effective amount of the composition to the subject. The route of administration of the pharmaceutical composition is selected from the group consisting of intravenous injection, intravenous infusion, intraperitoneal injection intraperitoneal infusion, intranasal, oral or any other route deemed appropriate by a practitioner. The therapeutically effective amount is in the range of 0.1 to 1,000 mg/kg. In some embodiments, the therapeutically effective amount is in the range of 1 to 500 mg/kg, 5 to 100 mg/kg, 10 to 50 mg/kg or 15 to 25 mg/kg. In one embodiment, the therapeutically effective amount is 0.5 mg/kg. In yet another embodiment, the therapeutically effective amount is 20 mg/kg. The treatment may be administered to a subject who is a human, a camel, a rodent, a primate, or any other subject susceptible to infection by MERS-CoV.

As used herein, the terms "MERS-CoV S", "MERS-CoV S protein" "MERS-CoV spike protein", "spike protein" and "S protein" are used interchangeably to refer to the spike protein of MERS-CoV. The S protein comprises two subunits, S1 and S2. As used herein, the term "S1 protein" is sometimes used to refer to the S1 subunit of the S protein but may also be used interchangeably when referring to the S protein, unless specifically identified otherwise.

As used herein, the terms "anti-S MERS-CoV", "anti-MERS-CoV S", and "MERS-CoV S antibodies" are used interchangeably to refer to antibodies against the MERS-CoV spike protein.

As used herein, the terms "antigen" and "immunogen" are used interchangeably. "Antigen" typically designates an entity or epitope that is bound by an antibody and the entity or epitope that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility. The terms "antigen", "antigenic region" The terms "peptide", "polypeptide" and "protein" may be used interchangeably herein, although a protein is typically a linear sequence of about 100 or more amino acids covalently joined by peptide bonds, a polypeptide is typically a linear sequence of about 55 to about 100 amino acids covalently joined by peptide bonds and a peptide is typically a linear sequence of about 55 or fewer amino acids covalently joined by peptide bonds.

The methods of the invention provide certain advantages over conventional treatments. For example, they can be produced naturally, i.e., using the immune system of chickens, thus avoiding complications or side effects that might arise from synthetic drugs. The safety profile for IgY antibodies is well-established. The antibodies can be raised against multiple antigenic targets, and this can reduce the probability of viral resistance. Another advantage is that being specific to the target pathogen, they will not affect the host microbiome of a subject who receives the IgY Abs, thus avoiding undesirable side effects associated with depletion or imbalance of host microbial populations. Furthermore, IgY Abs are not known to deposit in the muscle tissue, thus the ability to fight infections in animals avoids the possible defilements of protocols in several countries that prohibit the use of antibiotics in livestock industry for production of meat products.

The methods of the invention provide a non-invasive approach and pain-free animal-friendly technique for the production of antibodies in animals, since immunized hens will provide a steady supply of eggs from which the IgY Abs may be extracted. Large-scale production of IgY Abs can be attained by one chicken (about 22 g/year), with 2-10% of the antibodies being specifically targeted. Another advantage is the convenience of storage of the eggs, including long term storage of IgY Abs in eggs for as much as a year or more at 4° C. prior to isolation of the IgY Abs. Furthermore, the existing infrastructure of chicken farms for the large-scale production of eggs reduces the barriers for scale up the production of IgY Abs to an industrial scale.

The ability to store eggs long-term and/or to scale up production is yet another advantage of the invention. In cases of new viral outbreaks, IgY Abs can be produced within a short period of time (6 weeks from vaccination of hens) and can be formulated to provide immediate defense to individuals and the environment such as schools, airplanes and hospitals. The eggs can be stored in large quantities for global use in the time of pandemic.

After isolation from eggs, IgYs can be extremely stable at pH 4-9 and in hot conditions up to 65 degree Celsius in aqueous conditions. In the presence of pepsin, they can retain antigen-binding activity at pH 4-6, which demonstrates that they are very appropriate candidates for most types of processing and applications. The sialic acid high content in IgYs increases the half-life of the isolated antibodies, as compared to antibodies with low sialic acid content (Liu 2015). Without being bound by theory, this property may contribute to IgY-based therapy due to a long circulating half-life that increases the efficacy against the infections.

Yet another advantage of the invention is that low antigen quantities are needed to get an efficient immune response in chicken compared to the mammals commonly used for raising antibodies. It is also noteworthy that the performance of the antibodies of the invention is more efficacious compared to mammalian IgG-Abs, since IgY Abs have better binding avidity to the targeted antigens. The evolutionary distance between mammals and birds gives the IgY Abs the further advantage of producing antibodies against conserved mammalian proteins more easily and successfully than producing IgG-Abs in other mammals. Compared to mammalian IgG-Abs, IgY Abs does not activate or interact with mammalian Fc receptors or fix mammalian complement components, thus limiting the potential for inflammatory or dangerous immune responses in the subject receiving the IgY Abs treatment. Furthermore, there is no cross-reactivity with rheumatoid factors. For passive immunotherapy the IgY antibodies used can be given to a wide range of individuals belonging to any age and immunodeficient patients and pregnant women can be included.

The present invention also provides compositions for use in eliciting an immune response. The compositions may be utilized to immunize hens to produce IgY antibodies that prevent or treat MERS-CoV infection in mammals. By eliciting an immune response, we mean that administration of the antigen causes the synthesis of specific antibodies. The compositions include one or more isolated and substantially purified peptide or polypeptide as described herein, and a pharmacologically suitable carrier. The polypeptide(s) or protein(s) may be the same or different, i.e., the composition may be a "cocktail", or a composition containing only a single type of peptide or protein. The preparation of such compositions for use as immunogens is well known to those of skill in the art.

Pharmaceutical compositions comprising the anti-MERS-CoV S IgY Abs are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. The pharmaceutical compositions of the present invention may be administered as an oral form, wherein various thickeners, flavorings, diluents, emulsifiers, dispersing aids or binders and the like may be added. The composition of the present invention may contain any such additional ingredients so as to provide the composition in a form suitable for administration. The final amount of IgY Abs in the formulations may vary. However, in general, the amount in the formulations will be from about 0.01-99%, weight/volume. The amount of antibodies administered to a subject may range from 100 μg to 100,000 mg.

The methods involve administering a pharmaceutical composition comprising anti-MERS-CoV S IgY Abs in a pharmacologically acceptable carrier to a mammal. The mammal may be a human, but this need not always be the case, as veterinary applications of this technology are also contemplated. In particular, animals known to be vectors of MERS-CoV are contemplated, such as camels and other camelid species. Other species include but are not limited to companion "pets" such as dogs, cats, etc.; food source, work and recreational animals such as cattle, horses, oxen, sheep, pigs, goats, and the like; or even wild animals that may be found to serve as a reservoir of MERS-CoV. The pharmaceutical compositions of the present invention may be administered by any of the many suitable means which are well known to those of skill in the art, including but not limited to by injection, inhalation, orally, intranasally, by ingestion of a food product containing the anti-MERS-CoV S IgY Abs, etc. The mode of administration injection may be subcutaneous, intramuscular, intravenous or intraperitoneal. In addition, the compositions may be administered in conjunction with other treatment modalities such as substances that boost the immune system, various anti-bacterial chemotherapeutic agents, antibiotics, and the like.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene[1]polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention also encompasses antibodies to the epitopes and/or to the polypeptides disclosed herein. Such antibodies may be polyclonal, monoclonal or chimeric that are generated in chickens/eggs.

Before exemplary embodiments of the present invention are described in greater detail, it is to be understood that this invention is not limited to any particular embodiments described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Collectively, the following Examples of the invention demonstrate the use of anti-MERS-CoV S1 IgY for passive treatment of MERS-CoV infection in camels, humans and any other susceptible animal. Methods are provided for producing chicken egg yolk antibodies (IgY Abs) specific to the MERS-CoV spike protein that effectively neutralize MERS-CoV and treat or inhibit infection.

In some Examples, S1-specific immunoglobulins were produced by injecting chickens with purified recombinant S1 protein of MERS-CoV, a subunit of the full-length spike (S) protein, at a high titer (5.7 mg/mL egg yolk) at week 7 post immunization. Western blotting and immune-dot blot assays demonstrated that the IgY antibody specifically bound to the MERS-CoV S1 protein. Anti-S1 antibodies are also able to recognize MERS-COV inside cells, as demonstrated by immunofluorescence assay. Plaque reduction and microneutralization assays showed neutralization of MERS- COV in Vero cells by anti-S1 IgY antibodies and non-significantly reduced virus titers in the lungs of MERS-CoV-infected mice during early infection, with a nonsignificant decrease in weight loss. Less severe histological changes and reduced antigen expression in lung tissue were observed in subjects treated with anti-S1 IgY.

In other examples, S-specific IgY Abs were produced by injecting chickens with the purified recombinant S protein of MERS-CoV at a high titer (4.4 mg/mL per egg yolk) at week 7 post immunization. Western blotting and immune-dot blot assays demonstrated specific binding to the MERS-CoV S protein. In vitro neutralization of the generated IgY Abs against MERS-CoV was evaluated using a PCR-based assay and a 50% neutralizing concentration of 51.42 mg/ml. In vivo testing using a human-transgenic mouse model showed a reduction of viral antigen positive cells in treated mice, compared to the adjuvant-only controls. Moreover, the lung cells of the treated mice showed significantly reduced inflammation, compared to the controls. The results in the following Examples show efficient neutralization of MERS-CoV infection both in vitro and in vivo using S-specific IgY Abs.

These Examples describe materials and methods for using embodiments illustrated in FIGS. 1-14. Additional details can be found in the section entitled "Brief Description of the Drawings".

Example 1

Material and Methods
Immunization of Laying Hens
Eight Lohmann laying hens (25 weeks old) provided by a local broiler farm (Algharbia Breeding Company, Saudi Arabia) were used for egg production. Animals were placed in broiler chicken cages (two animals per cage) in a 12-hour light-dark cycle at room temperature (24±3° C.). Water and commercial laying hen food were offered ad libitum. The immunization group (n=4) was injected with 200 μg of a fragment of the recombinant MERS-CoV S protein obtained from Sino Biological, Inc. (China). The GenBank Accession number for this protein is AFS88936.1. The fragment used for immunizing animals is from Met1-Trp1297 of the full-length protein of AFS88936.1, having the amino acid identity shown in.

TABLE 1

Amino Acid sequence of immunogen

GenBank AFS88936.1 Met1-Trp1297 fragment    SEQ ID NO: 1
mihsvfllmflltptesyvdvgpdsvksacievdiqqtffdktwprpidvskadgiiypqgrtysniti
tyqglfpyqgdhgdmyvysaghatgttpqklfvanysqdvkqfangfvvrigaaanstgtviispst
satirkiypafmlgssvgnfsdgkmgrffnhtlvllpdgcgtllrafycileprsgnhcpagnsytsfat
yhtpatdcsdgnynrnaslnsfkeyfnlrnctfmytynitedeilewfgitqtaqgvhlfssryvdlyg
gnmfqfatlpvydtikyysiiphsirsiqsdrkawaafyvyklqpltflldfsvdgyirraidcgfndls
qlhcsyesfdvesgvysvssfeakpsgsvveqaegvecdfspllsgtppqvynfkrlvftncnynlt
kllslfsvndftcsqispaaiasncysslildyfsyplsmksdlsvssagpisqfnykqsfsnptclilat
vphnlttitkplkysyinkcsrllsddrtevpqlvnanqyspcvsivpstvwedgdyyrkqlsplegg
gwlvasgstvamteqlqmgfgitvqygtdtnsvcpklefandtkiasqlgncveyslygvsgrgvf
qnctavgvrqqrfvydayqnlvgyysddgnyyclracvsvpvsviydketkthatlfgsvacehis
stmsqysrstrsmlkrrdstygplqtpvgcvlglvnsslfvedcklplgqslcalpdtpstltprsvrsv
pgemrlasiafnhpiqvdqlnssyfklsiptnfsfgvtqeyiqttiqkvtvdckqyvcngfqkceqllr
eygqfcskinqalhganlrqddsvrnlfasvkssqsspiipgfggdfnltllepvsistgsrsarsaiedl
lfdkvtiadpgymqgyddcmqqgpasardlicaqyvagykvlpplmdvnmeaaytssllgsiag
vgwtaglssfaaipfaqsifyrlngvgitqqvlsenqkliankfnqalgamqtgftttneafqkvqda
vnnnaqalsklaselsntfgaisasigdiiqrldvleqdaqidrlingrlttlnafvaqqlvrsesaalsaq
lakdkvnecvkaqskrsgfcgqgthivsfvvnapnglyfmhvgyypsnhievvsayglcdaanp
tnciapvngyfiktnntrivdewsytgssfyapepitslntkyvapqvtyqnistnlpppllgnstgidf
qdeldeffknvstsipnfgsltqintlldltyemlslqqvvkalnesyidlkelgnytyynkwpw Injections were administered in the left or right side of the pectoral muscle on days 0, 14, 28, and 49. Before each immunization, the recombinant protein was emulsified in a 1:1 ratio with Freund's Complete Adjuvant (Sigma, USA) for the first immunization, and Freund's Incomplete Adjuvant (Sigma, USA,) was similarly used for subsequent booster immunizations. The suspension was mixed by pipetting up and down in a 19-gauge needle attached to a 5-ml syringe until stable. The control group (n=4) was injected with phosphate-buffered saline (PBS) plus the corresponding adjuvant. Blood samples were taken before each injection and on the day before slaughter. Eggs were collected daily 1 week before the initial immunization and continued for 12 weeks after immunization. Eggs were stored at 4° C. to isolate IgY from the yolk. The Biomedical Ethics Research Committee of the Faculty of Medicine at King Abdulaziz University reviewed and approved the experimental protocol (permit no: 120-18).

Isolation and Purification of Yolk IgY
Egg yolks from the harvested eggs of immunized and non-immunized hens were pooled and separated from egg whites using egg separators and then washed with deionized water. IgY purification was performed using a Pierce Chicken IgY Purification Kit (Thermo Fisher Scientific, USA). IgY concentration was determined via spectrophotometry measuring absorbance at 280 nm (A280) according to the manufacturer's instructions. Egg yolks were separated from the egg white using the Egg Separator, egg sacs were rolled onto a clean, dry paper towel to remove remaining egg white. The egg sacs were punctured with the Pasteur pipette and the egg yolks were collected. Egg yolks were mixed with five volumes of Delipidation Reagent with gentle continuous mixing. the sample mixtures were centrifuged for 15 minutes at 4000-10,000×g in a refrigerated centrifuge to remove the precipitated debris. While stirring gently, equal volume of cold IgY Precipitation Reagent was added to the supernatant, the mixture was centrifuged again after incubation for 1 hour at 4° C. PBS equal to the original volume of the egg yolk was added to the precipitated pellets that contained IgY and mixed gently until it is completely dissolved. The IgY concentration was determined using a NanoDrop 2000 spectrophotometer system (Thermo Scientific, USA. Cat: ND-2000C). IgY antibodies were filtered through a 0.45 μm filter and stored at −20° C.

Sodium Dodecyl Sulfate Polyacrylamide Gel Electrophoresis
Sodium dodecyl sulfate-polyacrylamide gel electrophoresis (SDS-PAGE) was performed to determine the purity and molecular weight of IgY using 12% PAGE with a Mini-PROTEAN® 3 cell (Bio-Rad Laboratories, USA). The analysis was conducted under reducing conditions: the sample was mixed with 2× sample buffer boiled for 10 minutes at 100° C., then 25 μl of purified IgY was loaded into each well. Pre-stained Blue Protein Marker (MOLEQULE-ON, New Zealand) was used as a molecular weight marker. Electrophoresis was performed at room temperature in running buffer (Tris-glycine buffer) at 200 volts for 40 minutes. Protein bands were visualized using Coomassie Brilliant Blue stain (Abcam; Cambridge, UK) and analyzed using Gene Tools image analysis software (Syngene, UK).

Reactivity of Anti-S IgY Antibodies by ELISA
The antibody reactivity of anti-S IgY was determined by ELISA. Briefly, microtiter plates were coated with purified MERS-CoV-S antigen (Sino Biological, Inc., China) at 500 ng/ml in PBS (0.01 M, pH 7.4) at 100 ml/well and then stored at 4° C. overnight. After washing the plates once with PBS and twice with Tween-20, they were blocked with 250 µl of blocking buffer (5% skim milk in PBS-Tween) at room temperature for 1 hour. The wells were washed three times with wash buffer. IgY antibody titers were determined by serially diluting the serum and purified IgY from immunized and non-immunized hens, starting with a 1:50 ratio in blocking buffer. The plates then were incubated at 37° C. for 1 hour and washed three times with PBS-Tween. A 1:10000 dilution of horseradish peroxidase (HRP)-conjugated rabbit anti-chicken IgY (Abcam, UK) was added to each well (100 µl/well) and incubated for 1 h at 37° C. After washing the plates, the color reaction was developed by adding TMB (100 µl/well) substrate solution (Promega, USA) and incubating for 30 minutes. This reaction was stopped by adding 2M H2SO4 (100 µl/well).

The optical density (OD) of each well was read at 450 nm using a microtiter plate reader (ELX800 Biokit). PBS was used as a blank control, and purified IgY derived from non-immunized hens was used as a negative control. The titer of anti-S IgY was defined as the maximum dilution of the sample that resulted in an OD value 2.1 times higher than that of the negative control.

Western Blotting Assay

Western blotting was performed to check the specificity of the anti-MERS-CoV S IgY antibody.

Five µl containing 500 ng of recombinant S protein was mixed with 20 µl of electrophoresis sample buffer and then subjected to SDS-PAGE in a 14% slab of polyacrylamide gel separated by a 4% stacking gel at 200V for 40 minutes at room temperature. The gel and blotting papers were equilibrated in transfer buffer for 10 minutes, after which the S protein was electrically transferred onto a polyvinylidene fluoride (PVDF) membrane activated by methanol (Thermo Fisher, USA) at 30V overnight. The PVDF membrane was cut into 0.5-cm strips, which were blocked with Tris-buffered saline containing 0.1% Tween 20 (TBS-T) and 5% non-fat dry milk for 1 hour at room temperature. The strips were washed three times for 10 minutes each. The membrane was then incubated in a 1:50 dilution of anti-MERS-CoV S IgY antibodies. After incubation, the strips were washed three times with TBS-T for 10 minutes each and incubated with HRP-conjugated rabbit anti-chicken IgY Heavy and Light (Abcam, UK) at a 1:10000 dilution in blocking buffer for 1 hour at room temperature. The strips again were washed three times for 10 minutes, after which they were incubated with HRP colorimetric substrate (Immun-Blot Opti-4CN colorimetric Kit, Bio-Rad) for 15 minutes at room temperature. This reaction was stopped by rinsing with distilled water. The strips were photographed after development.

Dot-Blotting

A dot-blot assay was performed to determine the specificity of the purified anti-S IgY antibodies. PVDF membranes were activated by soaking in methanol for 15 seconds and washing with distilled water. Then, three different concentrations (500, 100 and 50 ng) of the recombinant antigens S, S1, nucleocapsid, and PBD were dot-blotted individually onto a PVDF membrane. The membrane was incubated in 20 ml of blocking buffer for 1 hour at room temperature. After washing three times with TBS-T, the PVDF membrane was immersed in primary anti-MERS-CoV S IgY antibodies (1:200 dilution) in blocking buffer with gentle agitation for 1 hour at room temperature. The membrane was incubated with rabbit anti-chicken IgY HRP-conjugate as a secondary antibody (1:10000 dilution) in blocking buffer with gentle agitation for 1 hour at room temperature. After washing as previously described, the membrane was placed on an HRP colorimetric substrate (Immun-Blot Opti-4CN Colorimetric Kit, Cat. No. 1708235) for up to 30 minutes at room temperature. The reaction was stopped using distilled water.

Microneutralization Assay

Live virus experiments were performed in a biosafety level 3 laboratory in the infectious agent unit of King Fand Medical Research Center at King Abdulaziz University in Jeddah. A neutralizing assay was performed. Briefly, MERS-CoV isolate at an MOI of 0.01 (500 µL) in the presence or absence of IgY antibodies was added to an equal volume of serial dilutions of the IgY antibodies for 1 hour. The mixture was then inoculated in triplicate onto Vero E6 cells (10,000 cells/well) on 96-well plates and in viral inoculation medium (Dulbecco's Modified Eagle Medium with 2% fetal bovine serum, 1% penicillin/streptomycin, and 10 mmol/L HEPES at pH 7.2). Cells were incubated in a humidified incubator with 5% CO2 at 37° C. for 2-3 days or until reaching an 80-90% cytopathic effect (CPE) in virus-only positive control wells (virus with no added IgY Abs). The $IC_{100}$ neutralization of the antibody was determined as the reciprocal of the highest dilution at which no CPE was observed.

Assay of Neutralization Using Real-Time Quantitative RT-PCR

The MERS-CoV isolates at an MOI of 0.01 (500 µl) were added to an equal volume of varying dilutions of the IgY antibodies (440, 220, 110, 55, 44, 22, and 11 µg/ml). The mixture was then inoculated onto Vero cells (10,000 cells/well in triplicate) on 96-well plates and in the previously described viral inoculation medium. Cells were incubated in a humidified incubator with 5% CO2 at 37° C. for 2-3 days or until reaching 80-90% CPE in virus-only positive control wells (virus with no added IgY Abs).

Upon reaching 80-90% CPE in control wells, 200 µl of culture supernatants were collected, cleared by centrifugation (500×g, 5 minutes, 4° C.) and stored at −70° C. A negative control with no added virus or IgY was included in each experiment.

Real-time quantitative RT-PCR was performed using primers and probes targeting the MERS-CoV N gene, as previously described (Hindawi, Hashem et al. 2018), to assess the neutralization effect of the IgY antibodies. A neutralizing concentration of 50% was used to express IgY Ab neutralization activity and to define the concentration of IgY Ab needed to reduce the viral RNA copies by 50%, relative to the virus-only positive control.

Effect of Anti-S IgY Antibodies in Transgenic Mice Infected with MERS-CoV

A mouse model of MERS-CoV was used in this study, as previously described (Iwata-Yoshikawa, Okamura et al. 2019, Abbas, El-Kafrawy et al. 2020) Yoshikawa et al., JV, 2019).

Briefly, transgenic (Tg) mice on a C57BL/6NCr (SLC, Inc., Hamamatsu, Japan) background were developed to express human CD26/dipeptidyl peptidase 4 (hDPP4), a functional receptor for MERS-CoV under the control of an endogenous hDPP4 promoter. The hDPP4-Tg mice (n=10) were intranasally infected with MERS-CoV using the HCoV-EMC 2012 strain ($10^6$ $TCID_{50}$) provided by Dr. Bart Haagmans and Dr. Ron Fochier (Erasmus Medical Center, Rotterdam, the Netherlands). Mice also received a peritoneal injection of either 500 µg of anti-S IgY antibodies or 500 µg of IgY isotype control at 6 hours and 1 day post infection. This experiment was conducted simultaneously with that described in Example 2. Thus, data from the control mice are used in both Examples. Mouse weight was measured at 8 days post infection. Animals were sacrificed at 1 day, 3 days or 5 days post-infection (n=4), and lung tissues were collected for virological detection. After 8 days of observation, the remaining 6 mice were sacrificed for histopathological evaluations. All work with MERS-CoV and passive immunization of mice was conducted at the National Institute of Infectious Diseases in Tokyo, Japan. Stocks of MERS-CoV were propagated and titrated on Vero E6 cells and cryopreserved at −80° C. Viral infectivity titers were expressed as the $TCID_{50}$/ml on Vero E6 cells and calculated according to the Behrens-Kärber method. Work with infectious MERS-CoV was performed under biosafety level 3 conditions.

Histopathology and Immunohistochemistry

After anesthetizing and perfusing with 2 mL of 10% phosphate-buffered formalin, the mouse lungs were harvested and fixed in paraffin, sectioned, and subjected to hematoxylin and eosin staining. The tissue sections then were autoclaved at 121° C. for 10 minutes in a retrieval solution at pH 6.0 (Nichirei Biosciences Inc., Japan) for antigen retrieval in preparation for immunohistochemistry. MERS-CoV antigens were detected using a polymer-based detection system (Nichirei-Histofine Simple Stain Mouse MAX PO(R), Nichirei, Japan) with a rabbit anti-MERS-CoV nucleocapsid antibody (40068-RP01, Sino Biological Inc., Beijing, China). Peroxidase activity was detected using 3,3'-diaminobenzidine (Sigma-Aldrich), and hematoxylin was used for counterstaining.

Quantitative Analysis of Inflammation and Viral Antigen Positivity of Cells

Inflammation was assessed using hematoxylin and eosin staining on the paraffin-embedded sections (3-mm thickness) from the Tg mice at 8 days post infection. Light microscopic images were obtained using a DP71 digital camera under low-power magnification and cellSens software (Olympus Corporation, Tokyo, Japan) Inflammation was evaluated by measuring three lobes with an average section area of $3.645 \pm 0.726$ mm$^2$. The inflammation areas were traced using the contour measurement program Neurolucida (version 12, MBF Bioscience, Williston, Vt., USA) and analyzed using Neurolucida Explorer (MBF Bioscience). Viral antigen was detected via immunohistochemistry on a continuous paraffin-embedded section. Cells positive for viral antigen were counted in images under high-power magnification (observation area: 0.147 mm$^2$). Data for the control mice in this experiment is the same as that used in Example 2, which discloses another set of experiments assessing the efficacy of anti-S1 MERS-CoV IgY antibodies, as the two experiments were performed simultaneously.

Statistical Analysis

Data are expressed as means with standard errors. Statistical analyses were performed using Graph Pad Prism 9 software (GraphPad Software Inc., La Jolla, Calif., USA). Intergroup comparisons (virus titers in the lungs and body weight curves) were performed using two-way analyses of variance, followed by Bonferroni's multiple comparisons test. Comparisons between two groups (the quantitative analysis of inflammation and viral antigen positivity in cells) were performed using the Mann-Whitney test. A $p$ value of $<0.05$ was considered statistically significant.

Ethics Statement

The Biomedical Ethics Research Committee of the Faculty of Medicine at King Abdulaziz University reviewed and approved the experimental protocol for the immunization and handling of the chickens (permit no. 120-18). The Committee for Experiments Using Recombinant DNA and Pathogens at the National Institute of Infectious Diseases in Tokyo, Japan, approved the experiments using recombinant DNA and pathogens. Animal studies strictly followed the Guidelines for Proper Conduct of Animal Experiments of the Science Council of Japan and complied with animal husbandry and welfare regulations. All animals were housed in a facility certified by the Japan Health Sciences Foundation. Animal experiments also were approved by the Committee on Experimental Animals at the National Institute of Infectious Diseases in Japan, and all experimental animals were handled in accordance with biosafety level 3 animal facilities according to the committee guidelines.

Results

Isolation and Purification of IgY

Figure 1B:
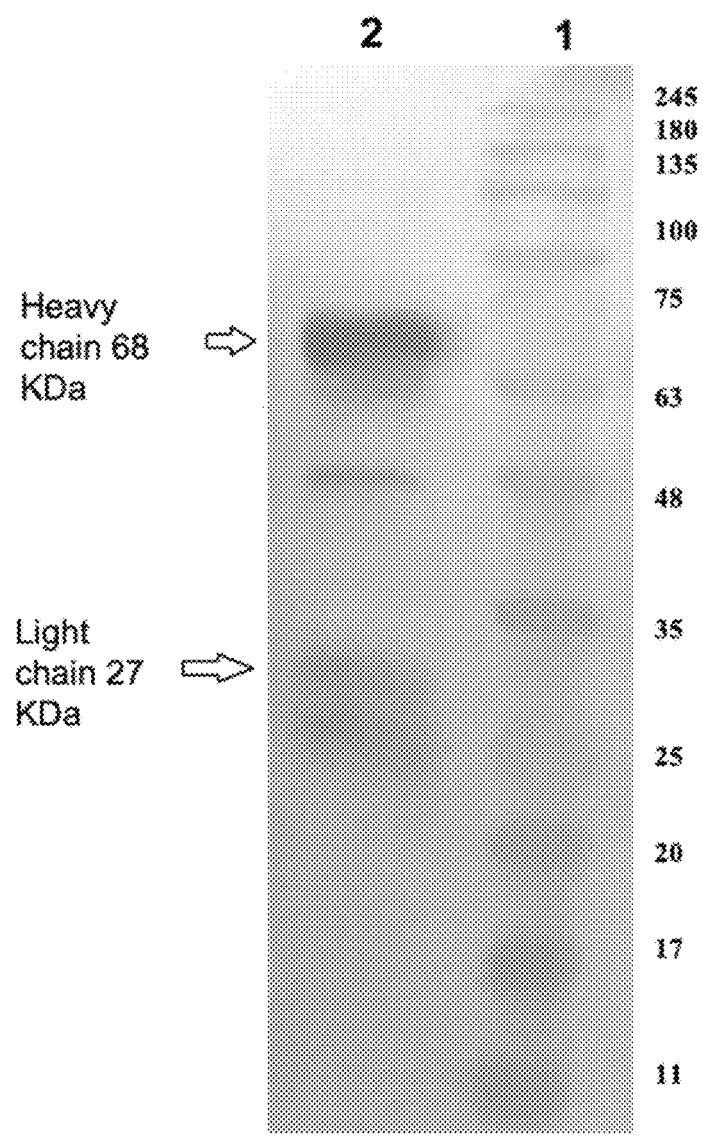

Western blotting and SDS-PAGE revealed that the IgY preparation dissociated into a major and minor protein band with molecular weights of ~68 kDa (heavy chain) and ~27 kDa (light chain), respectively, and a purity of 90%, as shown in FIGS. 1A and 1B. The total IgY contained in a milliliter of egg yolk was estimated to be 4.4 mg, or about 60 mg of total IgY from a single egg yolk (~15 ml).

Dynamics of Anti-S IgY Antibodies in the Sera of Chickens and Egg Yolks

Steady increases in serum levels of MERS-CoV S-specific IgY titers were observed in chicken sera after the first immunization. Levels peaked in week 7 and remained high until week 12. Sera of chickens who received the adjuvant only showed no reactivity to the MERS-CoV S antigen. Anti-MERS-CoV S antibody titers were not detected in the eggs until week 3 after immunization, then they increased until reaching a peak at week 7, and then plateaued until week 12, as shown in FIG. 2.

Immunoreactivity of Anti-S IgY of the MERS-COV

Figure 3A:
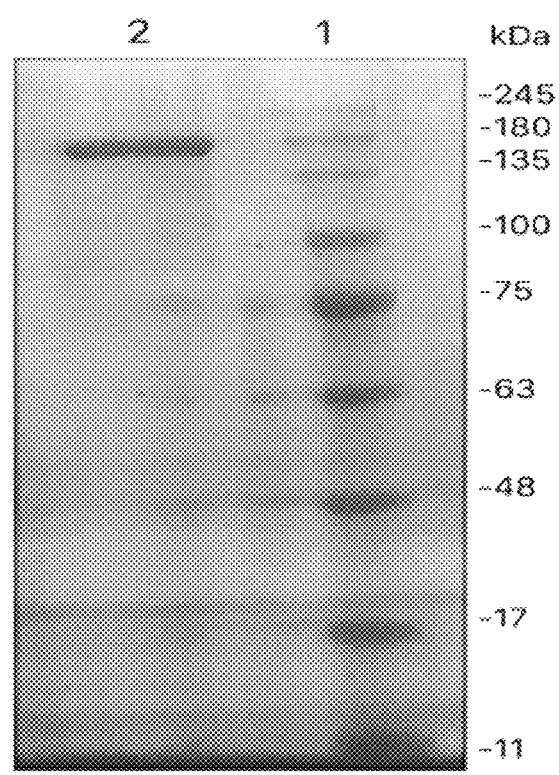
FIGS. 3A and 3B show SDS-PAGE and western blot analysis of anti-MERS-CoV S IgY antibodies.
Figure 3B:
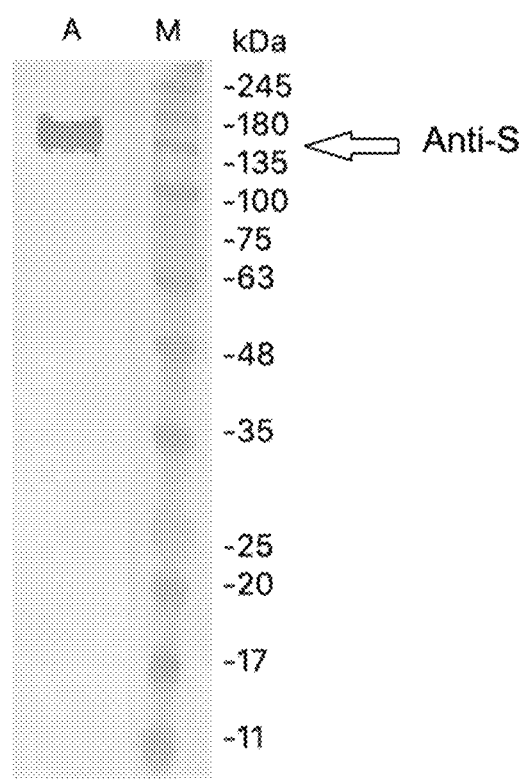

The specificity of anti-MERS-CoV S IgY antibodies was demonstrated using Western blotting, as shown in FIG. 3A, and SDS-PAGE analysis, shown in FIG. 3B. IgY antibodies induced by the S protein recognized the recombinant S protein at approximately 142 kDa.

Figure 4:
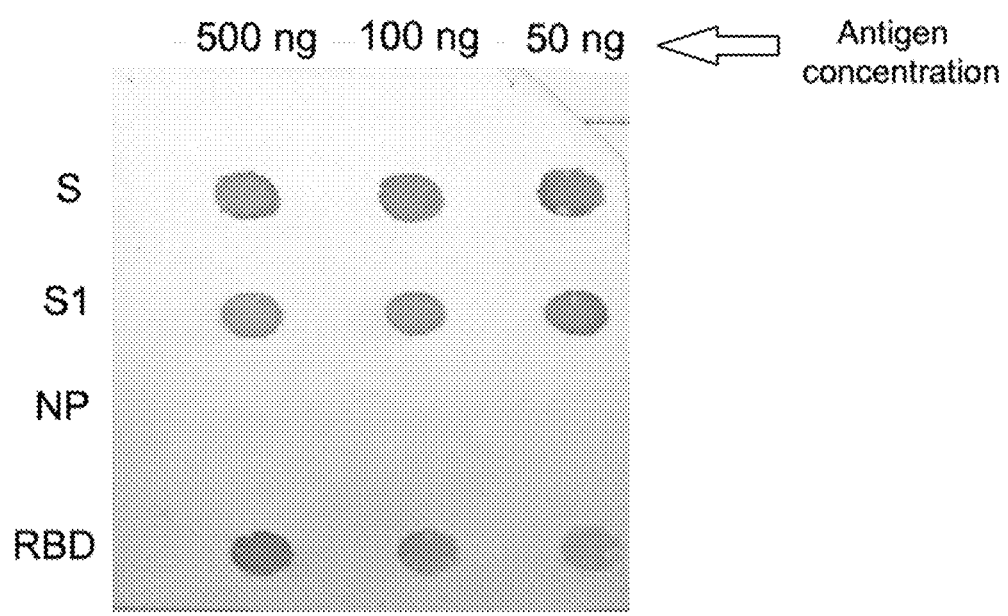
FIG. 4 shows dot-blot analysis of the anti-S IgY antibody binding. Purified anti-S IgY antibodies showed reactivity with different concentrations of the S, S1, and receptor-binding domain proteins but had no reactivity with the nucleocapsid protein of MERS-CoV.

The specificity of anti-S IgY antibodies was confirmed by dot blotting analysis. Purified IgY antibodies showed reactivity with the S protein, S1, and receptor-binding domain. The antibodies were not reactive to the nucleocapsid protein of MERS-CoV, as shown in FIG. 4.

Anti-S IgY Neutralizes MERS-CoV

Figure 5:
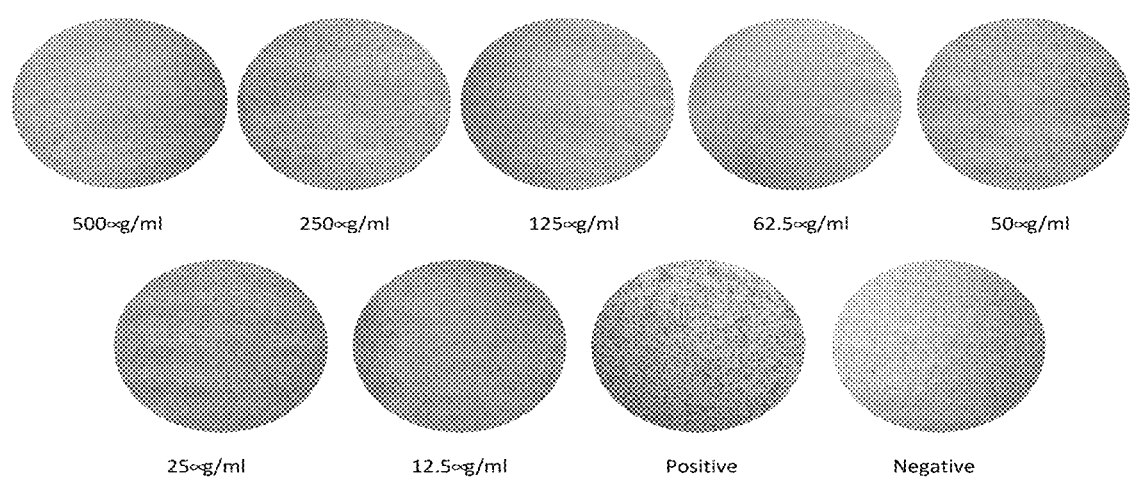
FIG. 5 shows the cytopathic effect of different concentrations of anti-S IgY antibodies against MERS-CoV in Vero-E6 cells. The $IC_{100}$ neutralization of the antibody was determined as the reciprocal of the highest dilution at which no cytopathic effect was observed.
Figure 6:
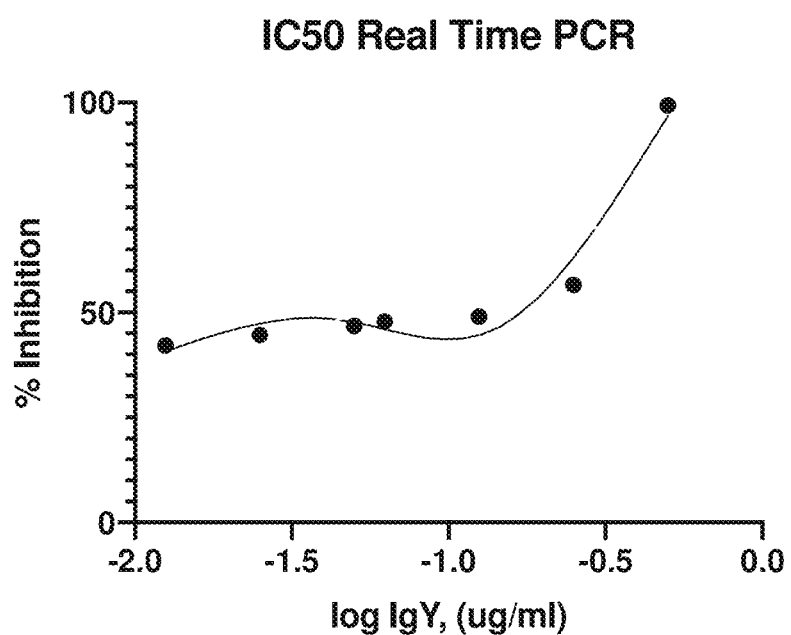
FIG. 6 shows a virus neutralization titer of a PCR-based virus neutralization test. IgY concentrations are represented in login (mg/ml).

Anti-S IgY can potently neutralize live MERS-CoV in permissive Vero cells, with 100% neutralization at $IC_{100}$ concentrations over 12.5 µg/mL. Nonspecific IgY Abs from adjuvant-only controls did not exhibit antiviral activity against MERS-CoV up to 1 mg/mL, as shown in FIG. 5. These results demonstrate that the anti-S MERS-CoV IgY antibodies exhibited a potent ability to neutralize MERS-CoV infection. $IC_{100}$ was determined as the reciprocal of the highest dilution at which no CPE was observed in the cells.

Quantitative Real Time RT-PCR-Based Neutralization Activity

The neutralization effect of the IgY Abs was examined by mixing different dilutions of the IgY Abs with MERS-CoV and then applying to the cells. This approach showed a high neutralization effect on the virus at a 50% neutralizing concentration (NCO of 51.42 mg/ml. The neutralization effect of the IgY Abs was assessed using quantitative real time RT-PCR of the cell cultures treated with different dilutions of the anti-MERS-CoV S IgY Abs, relative to the virus control cells (cells infected with the virus and untreated), which showed concentration-dependent inhibition of the virus in FIG. 6.

IgY Confers In Vivo Protection in Virus-Challenged Mice

Figure 7C:
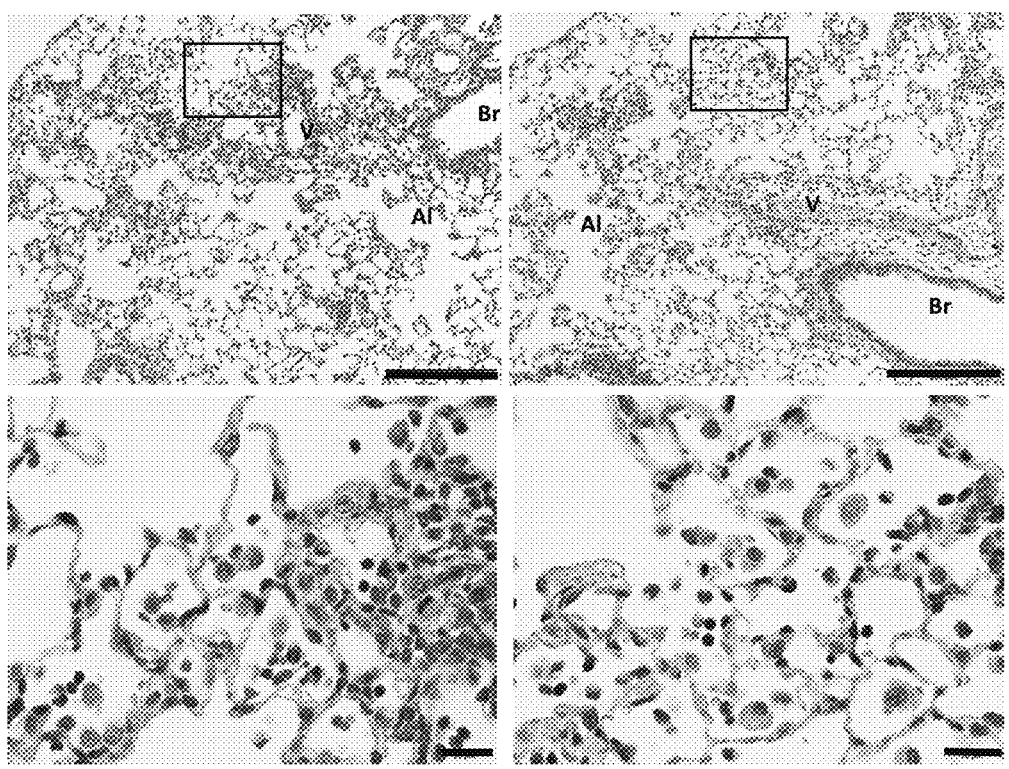
Figure 7D:
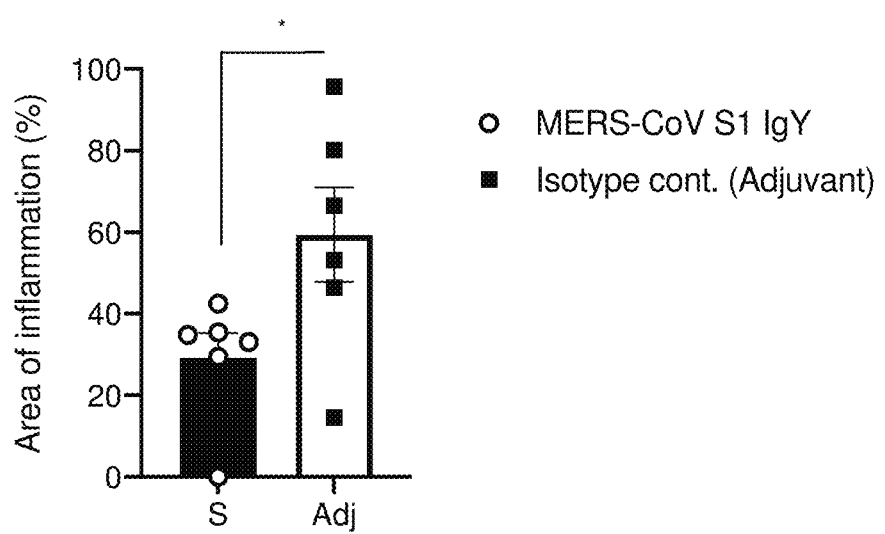
Figures 7E, 7F:
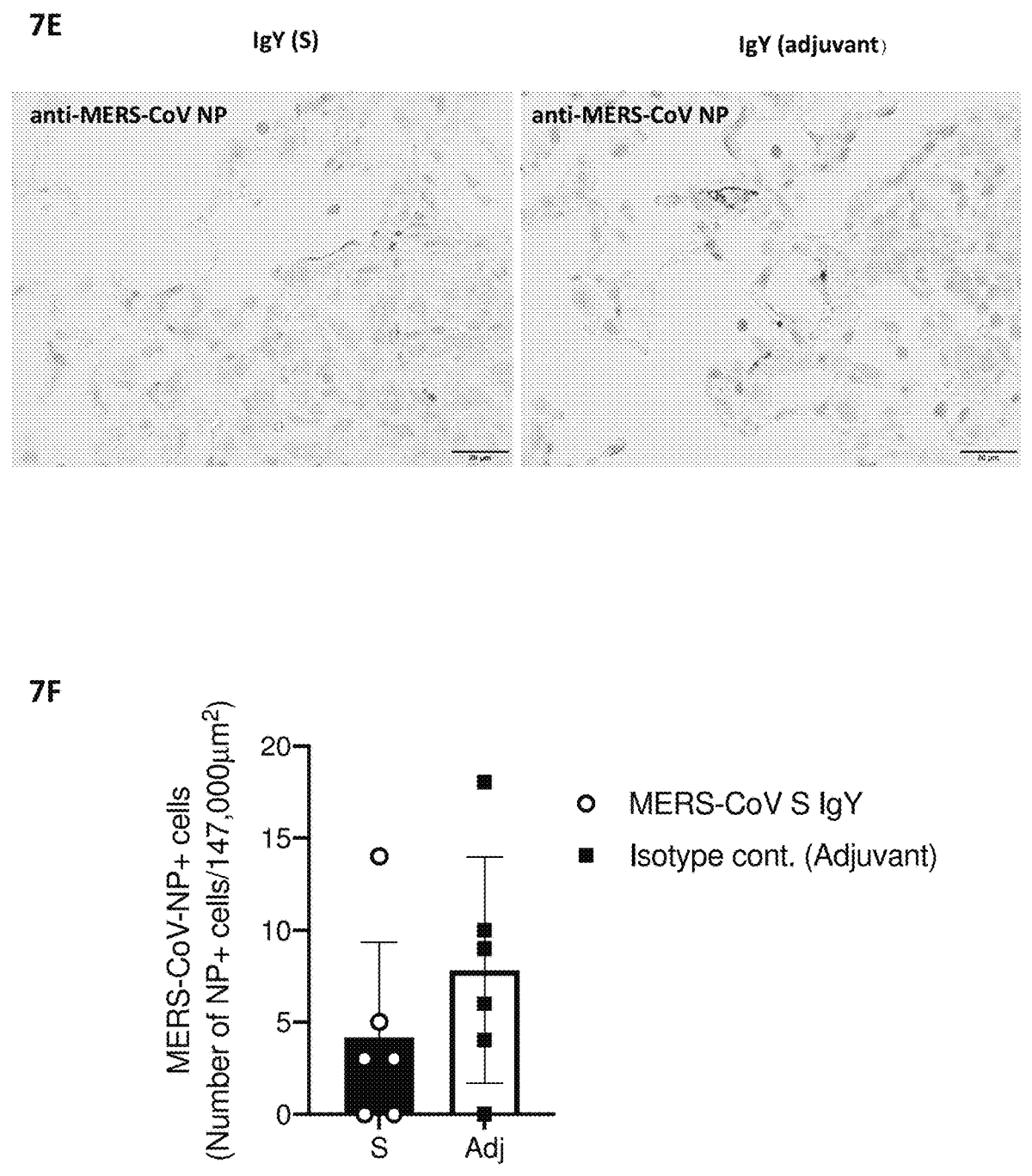

No significant difference was observed in the viral titers from the lungs of the anti-S IgY group, compared with the controls, as shown in FIG. 7A. Body weights of hDPP4-Tg mice were not significantly different between the MERS- CoV S IgY group and the adjuvant-only group after intranasal inoculation with $10^6$ TCID50 of MERS-CoV, shown in FIG. 7B. Histopathological investigations revealed that Tg mice developed progressive pulmonary inflammation due to acute MERS-CoV infection on day 8 post infection. FIG. 7C shows representative histological sections with inflammatory reactions, including partial and mild cellular infiltration with mononuclear cells and macrophages in response to viral infections, observed in the alveolar areas of the lung tissues from mice receiving anti-S IgY Abs, compared to non-specific IgY adjuvant-only control antibodies. Among virus-infected Tg mice, intraperitoneal injection of anti-S IgY antibodies led to significantly weaker inflammatory reactions ($p=0.041$), compared to the adjuvant-only control group, shown in FIG. 7C. FIG. 7D shows quantitation of the areas of inflammation in each group, with a statistically significant reduction in inflammation in mice receiving the MERS-CoV S IgY antibody treatment. FIG. 7E shows immunohistochemistry using an anti-MERS-CoV nucleocapsid polyclonal antibody in lung tissues, with fewer viral-antigen-positive cells in the lungs of the group treated with anti-S IgY compared with the adjuvant-only controls. FIG. 7D is a graphical representation of the reduction in the number of NP+ cells in the lungs from mice treated with MERS-CoV S IgY Abs, compared to the isotype control mice, who received IgY antibodies raised against adjuvant only.

Example 2

Some experiments described in Example 1 were also performed in Example 2. Experiments wherein conditions differed between the two Examples are noted as described below. Some assays were run simultaneously with Example 1 and are represented in Figures from Example 1, where indicated.
Materials and Methods
Immunization of Laying Hens
Four chickens (immunization group) were immunized by injection of 200 µg of recombinant MERS-CoV spike protein (S1) in the left and right side of pectoral muscle at days 0, 14, 28, and 49 (Met1-Glu725 of SEQ ID NO: 1 shown in Table 1; Sino Biological Inc, China Cat: 40069-V08H, AFS88936.1).
Isolation and Purification of Yolk IgY
IgY was isolated from egg yolks from immunized and nonimmunized hens as described for Example 1.
Sodium Dodecyl Sulfate-Polyacrylamide Gel Electrophoresis
Sodium dodecyl sulfate-polyacrylamide gel electrophoresis (SDS-PAGE) was performed to determine the purity and molecular weight of IgY as described for Example 1.
Reactivity of Anti-S1 IgY Antibodies
The reactivity and titer of the generated anti-S1 IgY antibodies was determined by ELISA as described for Example 1.
Western Blot Assay
In order to determine the specificity of the anti-MERS-CoV S1 IgY antibodies, western blotting was implemented as described for Example 1.
Immuno-Dot-Blot Assay
A dot-blot assay was performed to determine the specificity of the purified anti-S IgY antibodies using the protocol described for Example 1. Five hundred nanograms of each recombinant antigen (S, S1, nucleocapsid protein [NP], and receptor binding domain [RBD]) was separately dot-blotted onto PVDF membrane.

Immunofluorescence Assay
To perform the immunofluorescence assay, Vero cells were inoculated with MERS-CoV and the infected cells were harvested after 48 h of infection. The cells were collected by centrifugation at 1500 rpm for 5 min and washed twice with wash buffer consisting of 1 mL of BD Perm/Wash buffer (BD Biosciences, San Diego, USA Cat: 554723). One hundred microliters of the cell suspension were added to tubes containing 200 µL of blocking buffer (BD Cytofix/Cytoperm solution. Cat: 554714) and incubated for 1 h at room temperature. Cells were then washed twice with wash buffer.

The IgY antibodies were diluted to 570 µg/mL in Dulbecco's modified Eagle's medium (DMEM) supplemented with 2% fetal bovine serum (FBS). Two hundred microliters of the diluted anti-S1 IgY antibodies was added to each tube containing infected cells, followed by incubation for 1 h at room temperature. Cells were washed twice with wash buffer, and 100 µL of fluorescein isothiocyanate (FITC)-conjugated anti-chicken antibodies (Sigma, USA. Cat: F4137) was added (in a 1:2500 dilution) and incubated for 1 h at room temperature. Cells were washed twice with wash buffer, and 30 µL of cell suspension was fixed on a slide and observed under fluorescent microscope, and images were captured.
Neutralization Assay
Live virus experiments were performed in a Biosafety Level 3 laboratory of the Special Infections agent unit, King Fand Medical Research Center, King Abdulaziz University in Jeddah. Neutralizing assay was performed as described for Example 1.
Plaque Reduction Neutralization Test
Plaque reduction neutralization assay was performed to evaluate the neutralizing activity of anti-S1 IgY antibodies in MERS-CoV. Serial dilutions of the IgY antibodies were incubated with an equal volume of 0.01 MOI MERS-COV at 37° C. for 30 min. Subsequently, 200 µls of the incubated mixture were added to 95-100% confluent Vero E6 cells in 12-well plates. Each assay also included a cell control (PBS and cells) and a virus control (virus and cells). After 2 hours of incubation at 37° C., the surface of the Vero cells was covered with agarose-containing overlay medium of 1.5 mL to control indiscriminate spreading of the virus. plates were incubated for 72 h at 37° C. in a 5% carbon dioxide atmosphere. Vero cells were fixed with 10% formalin in phosphate-buffered saline followed by staining with 1% crystal violet in 50% ethanol. The 50% inhibitory concentration (IC50) of specific IgY against MERS-COV virus was evaluated via the Reed-Muench method (REED and MUENCH 1938)
Effect of Anti-S1 IgY Antibodies in Transgenic Mice after MERS-CoV Infection
The efficacy of anti-S1 IgY antibodies was tested in a mouse model of MERS-CoV as described for Example 1.
Histopathology and Immunohistochemistry
Lung tissues were obtained and analyzed as described in Example 1.
Results
Isolation and Purification of IgY
SDS-PAGE revealed that the IgY preparation dissociated into two protein bands, a major band at ~68 kDa (heavy chain) and a minor band at ~27 kDa (light chain) with 90% purity, as shown in FIG. 1. The total IgY contained in 1 mL of egg yolk was estimated to be 5.7 mg. Each egg yolk was approximately 15 mL, indicating that approximately 85.5 mg of total IgY could be obtained from a single egg.

Dynamics of Anti-S IgY Antibodies in Chickens' Sera and Egg Yolks

A steady increase in serum MERS-CoV S1-specific IgY titers was observed after the first immunization, reached a peak in week 7, and remained high until week 12. Sera of chickens immunized with PBS-adjuvant control did not show any reactivity to MERS-CoV-S. The anti-MERS-CoV S antibody titers in the eggs were not detected until the third week after immunization then started rising until reaching a peak in week 7. They plateaued at this level until week 12, as shown in FIG. 2.

Immunoreactivity of Anti-S1 IgY of the MERS-COV

Figure 8A:
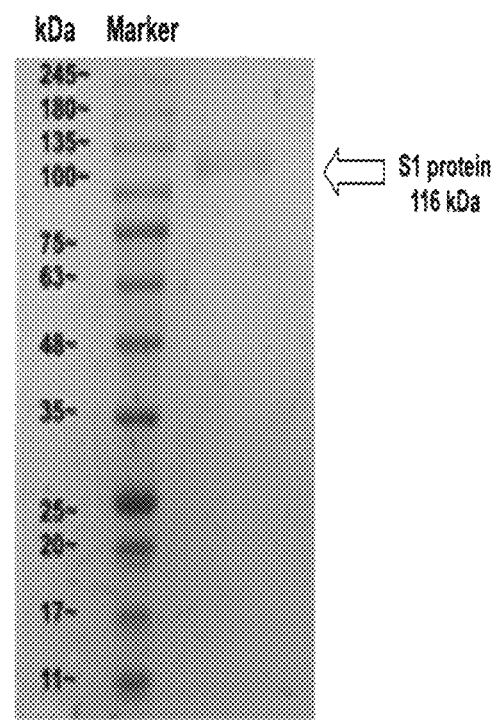
FIGS. 8A and 8B show Western blot analysis of anti-MERS-COV rS1 IgY antibodies and antibody response.
Figure 8B:
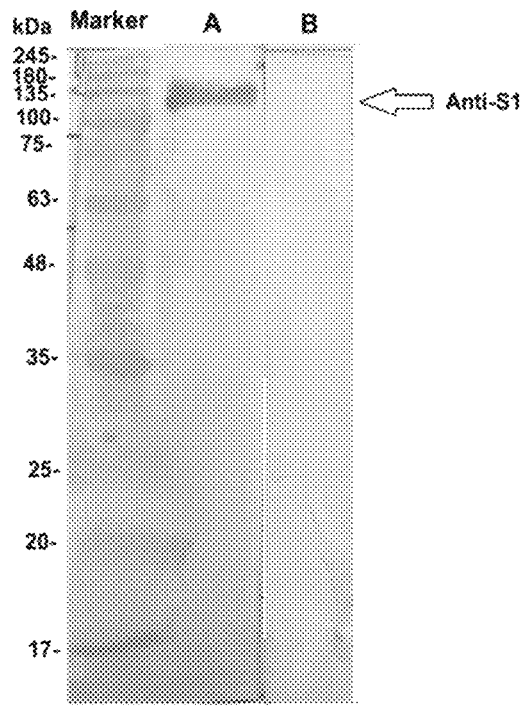

The specificities of anti-MERS-CoV S1-IgY antibodies were also tested by Western blot analysis. The IgY induced by MERS-CoV S1 was able to recognize the S protein at approximately 116 kDa (FIGS. 8A and 8B).

Dot Blotting

Figure 9:
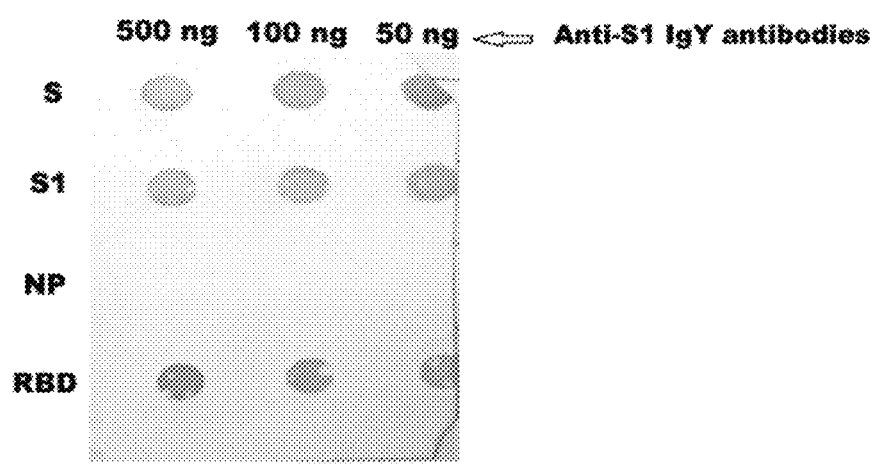
FIG. 9 shows a dot blotting analysis of purified anti-S1 IgY antibodies having reactivity with spike protein (S), S1, and receptor binding domain (RBD), but no reactivity with nucleocapsid (NP) protein of MERS CoV.

The specificities of anti-S1 IgY antibodies were also confirmed by dot immune-blot assay. Purified IgY antibodies showed reactivity with S, S1, and RBD, while no reactivity was observed with MERS CoV NP, as shown in FIG. 9.

Intracellular Immunofluorescent Detection of IgY Antibodies Binding to MERS-CoV

Figure 10:
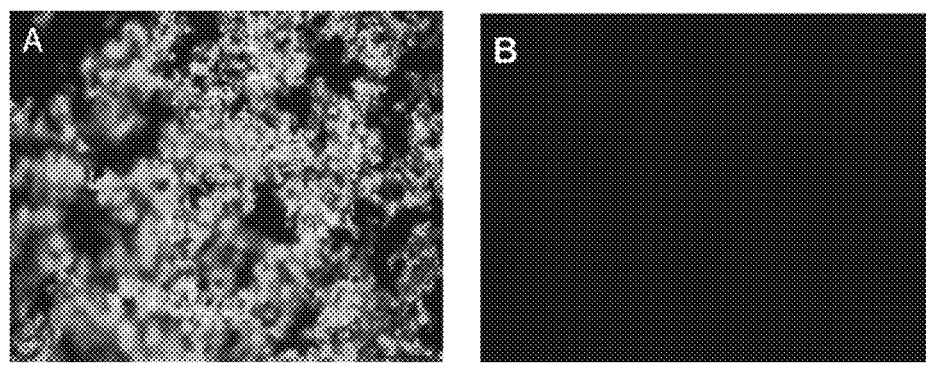
FIG. 10 shows recognition by anti-S1 IgY antibodies of viral antigen expressed in MERS-CoV-infected Vero E6 cells, using indirect immunofluorescence assay. Panel A is a representative image demonstrating the results of Vero E6 cells inoculated with MERS-CoV and stained with anti-S1 IgY antibodies and FITC-conjugated anti-chicken antibodies; and panel B shows control adjuvant IgY.

The intracellular binding of the generated IgY antibodies was confirmed by immunofluorescent staining of the IgY antibodies using FITC-labeled anti-chicken antibodies. Panel A of FIG. 10 shows a representative image of the cytoplasmic fluorescence of the treated cells indicating the binding of the IgY antibodies to the viral antigen inside the cells; cells with adjuvant IgY antibodies showed no fluorescence, as illustrated in panel B of FIG. 10.

Anti-S1 IgY Neutralizes MERS-CoV Infection

Figure 11:
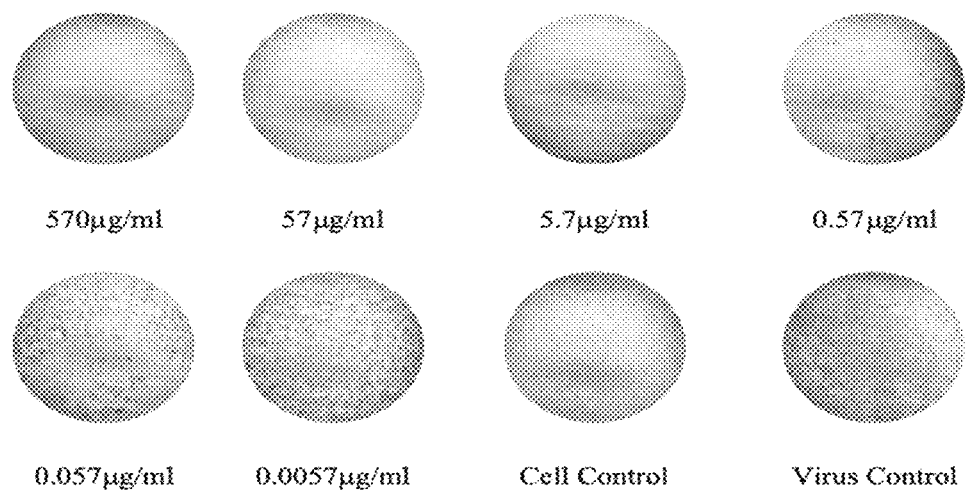
FIG. 11 shows examples of different concentrations of anti-S1 IgY antibodies tested against MERS-CoV on Vero-E6 cells examined by CPE.

Anti-S1 IgY could potently neutralize infection of live MERS-CoV in permissive Vero cells with 100% neutralization at concentration <31.2 µg/mL, whereas nonspecific antibodies from adjuvant-immunized chickens did not exhibit antiviral activity against MERS-CoV infection up to 1 mg/mL, as shown in FIG. 11. These results demonstrate that anti-S1 MERS-CoV IgY antibodies have a potent ability to neutralize MERS-CoV infection.

IgY Inhibits Virus Replication In Vitro

Figure 12A:
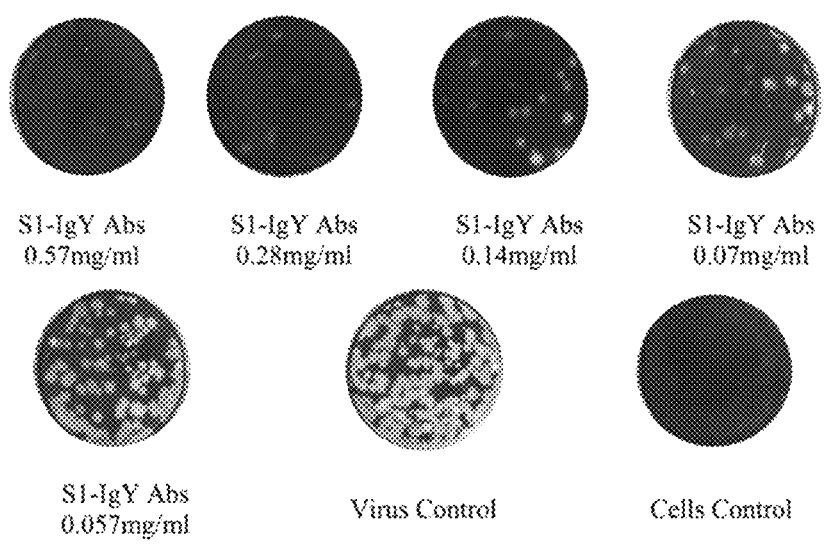
FIGS. 12A and 12B show evaluation of the neutralizing potential of anti-S1 IgY antibodies, using plaque reduction neutralization test.
Figure 12B:
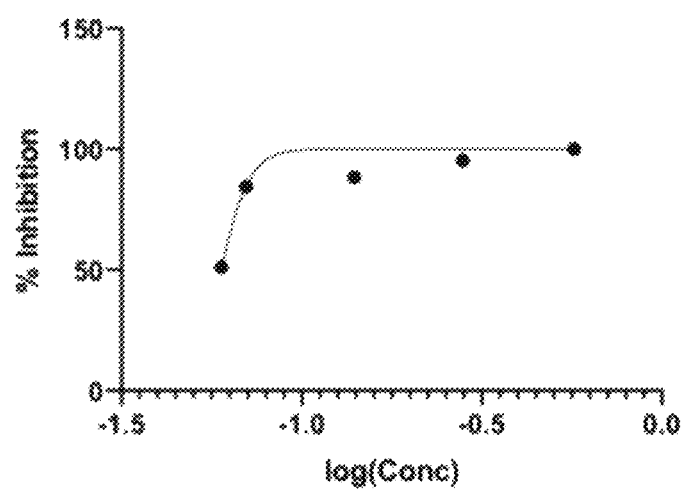

To further confirm the antiviral activity observed with the above neutralization assay, a plaque reduction assay was performed on Vero E6 cells inoculated with MERS-CoV pre-incubated with IgY antibodies. As shown in FIG. 12A, the specific IgY significantly inhibited MERS-CoV virus replication in Vero cells with an IC50 of 0.06 mg/mL, as quantitated in FIG. 12B.

IgY Confers In Vivo Protection in Virus-Challenged Mice

Next, we determined the effect of anti-S1 IgY treatment in vivo. Intraperitoneal treatment with anti-S1 IgY antibodies resulted in no significant difference in the viral titer in the lung compared with the control adjuvant IgY, but the titer was slightly lower at day 3 post infection in the anti-S1 IgY group compared with the control group, shown in FIG. 13A.

Figures 13A, 13B:
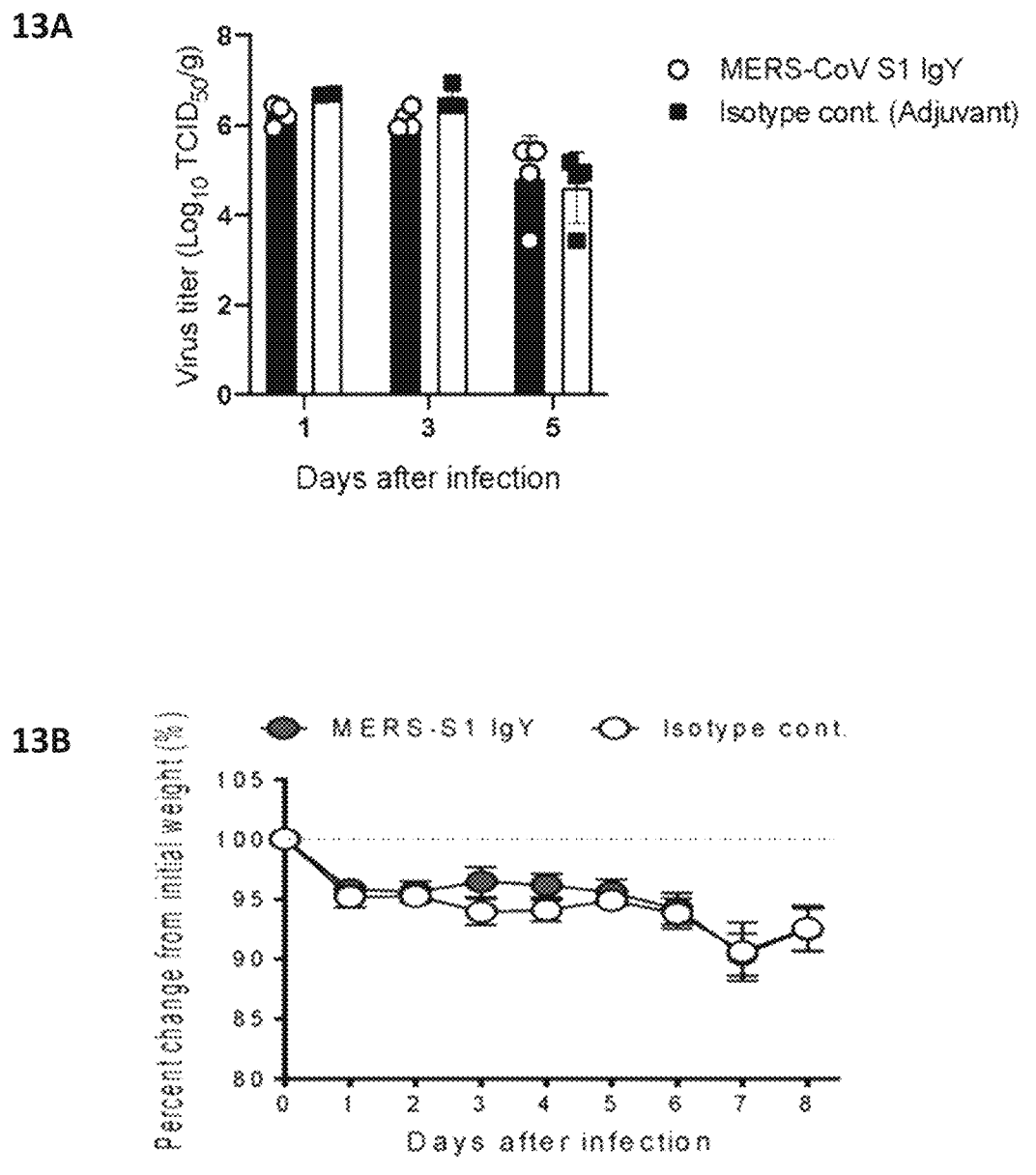

Body weight changes were not significantly different after intranasal inoculation with $10^6$ $TCID_{50}$ of MERS-CoV in hDPP4-Tg mice between MERS-CoV S1 IgY antibodies and control adjuvant IgY groups, as shown in FIG. 13B.

Figure 14:
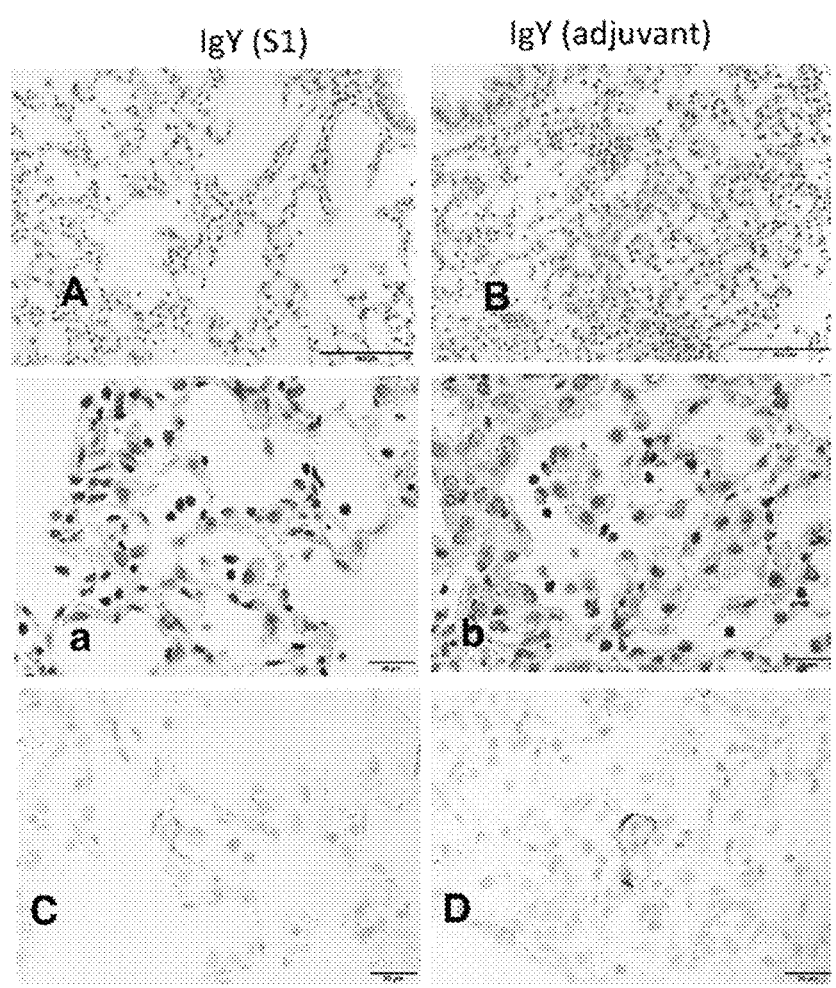
FIG. 14 shows representative images of histopathological changes in the lungs of human dipeptidyl peptidase 4 (hDPP4)-transgenic mice infected with MERS-CoV on day 8 post inoculation. Lungs were fixed in neutral-buffered 10% formalin, and sections were stained with hematoxylin and eosin. Scale bars: 100 µm in Panels A and B; Scale bars: 20 µm in Panels a and b. Representative histopathological findings of mice with the highest cellular infiltration in alveoli. Mononuclear cell infiltrations including macrophages and lymphocytes occurred in the alveolar area in the adjuvant control group (Panels B and b) compared with lower inflammatory infiltrations in the anti-S1 IgY-treated group (Panels A and a). Detection of viral antigen in lung tissues of mice by immunohistochemistry is shown in Panels C and D). A few antigen-positive cells were seen in the lungs of the anti-S1 IgY-treated group (Panel C) compared with the adjuvant control group (Panel D). Scale bars in Panels C and D: 20 µm.

Histopathological investigations revealed that Tg mice showed progressive pulmonary inflammation associated with acute viral infection on day 8 post infection, illustrated with representative images in FIG. 14. Inflammatory reactions, including partial and/or mild cellular infiltration with mononuclear cells and macrophages in response to viral infections, were observed in alveolar areas of lung tissue (Panels A and a), but interestingly, the group treated with anti-S1 IgY antibodies showed a markedly decreased inflammatory reaction compared with the control group (Panels B and b). Moreover, IHC using an anti-MERS-CoV NP polyclonal antibody in lung tissues revealed a few antigen-positive cells in the lungs of the anti-S1 IgY-treated group (Panel C) compared with the adjuvant IgY control group (Panel D).

REFERENCES

Abbas, A. T., S. A. El-Kafrawy, S. S. Sohrab, A. A. Tabll, A. M. Hassan, N. Iwata-Yoshikawa, N. Nagata and E. I. Azhar (2020). "Anti-S1 MERS-COV IgY Specific Antibodies Decreases Lung Inflammation and Viral Antigen Positive Cells in the Human Transgenic Mouse Model." *Vaccines (Basel)* 8(4).

Corti, D., J. Zhao, M. Pedotti, L. Simonelli, S. Agnihothram, C. Fett, B. Fernandez-Rodriguez, M. Foglierini, G. Agatic and F. Vanzetta (2015). "Prophylactic and postexposure efficacy of a potent human monoclonal antibody against MERS coronavirus." *Proceedings of the National Academy of Sciences* 112(33): 10473-10478.

Corti, D., J. Zhao, M. Pedotti, L. Simonelli, S. Agnihothram, C. Fett, B. Fernandez-Rodriguez, M. Foglierini, G. Agatic, F. Vanzetta, R. Gopal, C. J. Langrish, N. A. Barrett, F. Sallusto, R. S. Baric, L. Varani, M. Zambon, S. Perlman and A. Lanzavecchia (2015). "Prophylactic and postexposure efficacy of a potent human monoclonal antibody against MERS coronavirus." *Proc Natl Acad Sci USA* 112(33): 10473-10478.

Ferella, A., D. Bellido, P. Chacana, A. Wigdorovitz, M. J. D. Santos and M. V. Mozgovoj (2012). "Chicken egg yolk antibodies against bovine respiratory syncytial virus neutralize the virus in vitro." *Procedia in Vaccinology* 6(Supplement C): 33-38.

Fu, C. Y., H. Huang, X. M. Wang, Y. G. Liu, Z. G. Wang, S. J. Cui, H. L. Gao, Z. Li, J. P. Li and X. G. Kong (2006). "Preparation and evaluation of anti-SARS coronavirus IgY from yolks of immunized SPF chickens." *J Virol Methods* 133(1): 112-115.

Gadde, U., T. Rathinam and H. S. Lillehoj (2015). "Passive immunization with hyperimmune egg-yolk IgY as prophylaxis and therapy for poultry diseases—A review." *Anim Health Res Rev* 16(2): 163-176.

Hindawi, S. I., A. M. Hashem, G. A. Damanhouri, S. A. El-Kafrawy, A. M. Tolah, A. M. Hassan and E. I. Azhar (2018). "Inactivation of Middle East respiratory syndrome-coronavirus in human plasma using amotosalen and ultraviolet A light." *Transfusion* 58(1): 52-59.

Ikemori, Y., R. C. Peralta, M. Kuroki, H. Yokoyama and Y. Kodama (1993). "Research note: avidity of chicken yolk antibodies to enterotoxigenic *Escherichia coli* fimbriae." *Poult Sci* 72(12): 2361-2365.

Iwata-Yoshikawa, N., T. Okamura, Y. Shimizu, O. Kotani, H. Sato, H. Sekimukai, S. Fukushi, T. Suzuki, Y. Sato, M. Takeda, M. Tashiro, H. Hasegawa and N. Nagata (2019). "Acute Respiratory Infection in Human Dipeptidyl Peptidase 4-Transgenic Mice Infected with Middle East Respiratory Syndrome Coronavirus." *J Virol* 93(6).

Jahangiri, A., P. Owlia, I. Rasooli, J. Salimian, E. Derakhshanifar, A. Naghipour Erami, E. Darzi Eslam and S. Darvish Alipour Astaneh (2018). "Specific egg yolk antibodies (IgY) confer protection against *Acinetobacter baumannii* in a murine pneumonia model." *J Appl Microbiol*.

Kollberg, H., D. Carlander, H. Olesen, P. E. Wejaker, M. Johannesson and A. Larsson (2003). "Oral administration of specific yolk antibodies (IgY) may prevent *Pseudomo-* nas aeruginosa infections in patients with cystic fibrosis: a phase I feasibility study." *Pediatr Pulmonol* 35(6): 433-440.

Landry, M. L. and K. St. George (2017). "Laboratory diagnosis of Zika virus infection." *Archives of pathology & laboratory medicine* 141(1): 60-67.

Li, F. (2015). "Receptor recognition mechanisms of coronaviruses: a decade of structural studies." *J Virol* 89(4): 1954-1964.

Li, X., L. Wang, Y. Zhen, S. Li and Y. Xu (2015). "Chicken egg yolk antibodies (IgY) as non-antibiotic production enhancers for use in swine production: a review." *J Anim Sci Biotechnol* 6(1): 40.

Li, Y., Y. Wan, P. Liu, J. Zhao, G. Lu, J. Qi, Q. Wang, X. Lu, Y. Wu, W. Liu, B. Zhang, K. Y. Yuen, S. Perlman, G. F. Gao and J. Yan (2015). "A humanized neutralizing antibody against MERS-CoV targeting the receptor-binding domain of the spike protein." *Cell Res* 25(11): 1237-1249.

Liu, L. (2015). "Antibody glycosylation and its impact on the pharmacokinetics and pharmacodynamics of monoclonal antibodies and Fc-fusion proteins." *J Pharm Sci* 104(6): 1866-1884.

Lu, G., Y. Hu, Q. Wang, J. Qi, F. Gao, Y. Li, Y. Zhang, W. Zhang, Y. Yuan, J. Bao, B. Zhang, Y. Shi, J. Yan and G. F. Gao (2013). "Molecular basis of binding between novel human coronavirus MERS-CoV and its receptor CD26." *Nature* 500(7461): 227-231.

Nguyen, H. H., T. M. Tumpey, H. J. Park, Y. H. Byun, L. D. Tran, V. D. Nguyen, P. E. Kilgore, C. Czerkinsky, J. M. Katz, B. L. Seong, J. M. Song, Y. B. Kim, H. T. Do, T. Nguyen and C. V. Nguyen (2010). "Prophylactic and therapeutic efficacy of avian antibodies against influenza virus H5N1 and H1N1 in mice." *PLoS One* 5(4): e10152.

Otterbeck, A., K. Hanslin, E. L. Lantz, A. Larsson, J. Stalberg and M. Lipcsey (2019). "Inhalation of specific anti-*Pseudomonas aeruginosa* IgY antibodies transiently decreases *P. aeruginosa* colonization of the airway in mechanically ventilated piglets." *Intensive Care Med Exp* 7(1): 21.

Pauly, D., M. Dorner, X. Zhang, A. Hlinak, B. Dorner and R. Schade (2009). "Monitoring of laying capacity, immunoglobulin Y concentration, and antibody titer development in chickens immunized with ricin and botulinum toxins over a two-year period." *Poult Sci* 88(2): 281-290.

Raj, V. S., H. Mou, S. L. Smits, D. H. Dekkers, M. A. Muller, R. Dijkman, D. Muth, J. A. Demmers, A. Zaki, R. A. Fouchier, V. Thiel, C. Drosten, P. J. Rottier, A. D. Osterhaus, B. J. Bosch and B. L. Haagmans (2013). "Dipeptidyl peptidase 4 is a functional receptor for the emerging human coronavirus-EMC." *Nature* 495(7440): 251-254.

REED, L. J. and H. MUENCH (1938). "A SIMPLE METHOD OF ESTIMATING FIFTY PERCENT END-POINTS12." *American Journal of Epidemiology* 27(3): 493-497.

Sabir, J. S., T. T. Lam, M. M. Ahmed, L. Li, Y. Shen, S. E. Abo-Aba, M. I. Qureshi, M. Abu-Zeid, Y. Zhang, M. A. Khiyami, N. S. Alharbi, N. H. Hajrah, M. J. Sabir, M. H. Mutwakil, S. A. Kabli, F. A. Alsulaimany, A. Y. Obaid, B. Zhou, D. K. Smith, E. C. Holmes, H. Zhu and Y. Guan (2016). "Co-circulation of three camel coronavirus species and recombination of MERS-CoVs in Saudi Arabia." *Science* 351(6268): 81-84.

Sharma, J. M. (1999). "Introduction to poultry vaccines and immunity." *Adv Vet Med* 41: 481-494.

Sudjarwo, S. A., K. Eraiko, G. W. Sudjarwo and Koerniasari (2017). "The potency of chicken egg yolk immunoglobulin (IgY) specific as immunotherapy to *Mycobacterium tuberculosis* infection." *J Adv Pharm Technol Res* 8(3): 91-96.

Traggiai, E., S. Becker, K. Subbarao, L. Kolesnikova, Y. Uematsu, M. R. Gismondo, B. R. Murphy, R. Rappuoli and A. Lanzavecchia (2004). "An efficient method to make human monoclonal antibodies from memory B cells: potent neutralization of SARS coronavirus." *Nature medicine* 10(8): 871-875.

Tsukamoto, M., S. Hiroi, K. Adachi, H. Kato, M. Inai, I. Konishi, M. Tanaka, R. Yamamoto, M. Sawa, E. Handharyani and Y. Tsukamoto (2011). "Antibodies against swine influenza virus neutralize the pandemic influenza virus A/H1N1." *Mol Med Rep* 4(2): 209-214.

Wallach, M. G., R. J. Webby, F. Islam, S. Walkden-Brown, E. Emmoth, R. Feinstein and K. O. Gronvik (2011). "Cross-Protection of Chicken Immunoglobulin Y Antibodies against H5N1 and H1N1 Viruses Passively Administered in Mice." *Clinical and Vaccine Immunology* 18(7): 1083-1090.

Walls, A. C., Y.-J. Park, M. A. Tortorici, A. Wall, A. T. McGuire and D. Veesler (2020). "Structure, function, and antigenicity of the SARS-CoV-2 spike glycoprotein." *Cell*.

Wen, J. L., S. Q. Zhao, D. G. He, Y. N. Yang, Y. M. Li and S. S. Zhu (2012). "Preparation and characterization of egg yolk immunoglobulin Y specific to influenza B virus." *Antiviral Research* 93(1): 154-159.

Widjaja, I., C. Wang, R. van Haperen, J. Gutierrez-Alvarez, B. van Dieren, N. M. A. Okba, V. S. Raj, W. Li, R. Fernandez-Delgado, F. Grosveld, F. J. M. van Kuppeveld, B. L. Haagmans, L. Enjuanes, D. Drabek and B. J. Bosch (2019). "Towards a solution to MERS: protective human monoclonal antibodies targeting different domains and functions of the MERS-coronavirus spike glycoprotein." *Emerg Microbes Infect* 8(1): 516-530.

Xu, Y., X. Li, L. Jin, Y. Zhen, Y. Lu, S. Li, J. You and L. Wang (2011). "Application of chicken egg yolk immunoglobulins in the control of terrestrial and aquatic animal diseases: a review." *Biotechnol Adv* 29(6): 860-868.

Yang, Y. E., J. L. Wen, S. Q. Zhao, K. Zhang and Y. L. Zhou (2014). "Prophylaxis and therapy of pandemic H1N1 virus infection using egg yolk antibody." *Journal of Virological Methods* 206: 19-26.

Yi, L., Z. Qin, H. Lin, Y. Zhou, J. Li, Z. Xu, V. S. Babu and L. Lin (2018). "Features of chicken egg yolk immunoglobulin (IgY) against the infection of red-spotted grouper nervous necrosis virus." *Fish Shellfish Immunol* 80: 534-539.

Zhao, J., K. Li, C. Wohlford-Lenane, S. S. Agnihothram, C. Fett, J. Zhao, M. J. Gale, Jr., R. S. Baric, L. Enjuanes, T. Gallagher, P. B. McCray, Jr. and S. Perlman (2014). "Rapid generation of a mouse model for Middle East respiratory syndrome." *Proc Natl Acad Sci USA* 111(13): 4970-4975.

Zhao, J., R. A. Perera, G. Kayali, D. Meyerholz, S. Perlman and M. Peiris (2015). "Passive immunotherapy with dromedary immune serum in an experimental animal model for Middle East respiratory syndrome coronavirus infection." *J Virol* 89(11): 6117-6120.

Zhao, Y., C. Wang, B. Qiu, C. Li, H. Wang, H. Jin, W. Gai, X. Zheng, T. Wang, W. Sun, F. Yan, Y. Gao, Q. Wang, J. Yan, L. Chen, S. Perlman, N. Zhong, J. Zhao, S. Yang and X. Xia (2017). "Passive immunotherapy for Middle East Respiratory Syndrome coronavirus infection with equine immunoglobulin or immunoglobulin fragments in a mouse model." *Antiviral Res* 137: 125-130.

Thus, the foregoing Examples of the invention provide enablement for producing IgY antibodies in chicken eggs for treatment or prevention of MERS-CoV infection, with the advantages of:

Easy to produce and sample the antibody levels in eggs
Can be produced in large batches
Low cost, non-invasive, and high amounts of antibody can be obtained
Remains stable at variable pH and temperatures
Performs better at recognition of conserved mammalian epitopes than IgGs
Detects small changes within antigens
Can identify various epitopes on a given antigen
No activation of the mammalian complement
No cross-reactivity with rheumatoid factors While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

---

We claim:

1. A method of producing immunoglobulin Y (IgY) antibodies against Middle Eastern respiratory syndrome coronavirus (MERS-CoV), comprising the steps of:
   a) immunizing chicken hens with about 200 µg of peptide at about days 0, 14, 28, and 49, wherein said peptide comprises at least one immunogenic domain of a spike protein from the MERS-CoV, and
   b) isolating the IgY antibodies against the MERS-CoV spike protein from yolks of eggs laid by the immunized hens.

2. The method of claim 1, wherein the peptide has the amino acid identity of SEQ ID NO:1.

3. The method of claim 1, wherein the peptide has the amino acid identity of Met1-Glu725 of SEQ ID NO:1.

4. A method of inhibiting or treating a Middle Eastern respiratory syndrome coronavirus (MERS-CoV) infection in a subject in need thereof, comprising the steps of:
   a) isolating IgY antibodies to a MERS-CoV spike peptide according to the method of claim 1;
   b) preparing a pharmaceutically acceptable composition comprising the IgY antibodies from step a); and
   c) administering a therapeutically effective amount of the pharmaceutically acceptable composition of step b) to the subject.

5. The method of claim 4, wherein the peptide has the amino acid sequence identity of SEQ ID NO:1.

6. The method of claim 4, wherein the peptide has the amino acid sequence identity of Met1-Glu725 of SEQ ID NO:1.

7. The method of claim 4, wherein the route of administration in step c) of the pharmaceutically acceptable composition is selected from the group consisting of intravenous injection, intravenous infusion, intraperitoneal injection, intraperitoneal infusion, intranasal and oral.

8. The method of claim 4, wherein the therapeutically effective amount is in the range of 0.1 to 1,000 mg/kg.

9. The method of claim 4, wherein the route of administration in step c) of the pharmaceutically acceptable composition is by intravenous injection or infusion.

10. The method of claim 4, wherein the subject is a camel.

11. The method of claim 4, wherein the subject is a human.

12. A method of inhibiting or treating a Middle Eastern respiratory syndrome coronavirus (MERS-CoV) infection in a subject in need thereof, comprising the steps of:
   a) injecting chicken hens with about 200 µg of a peptide at about days 0, 14, 28, and 49, wherein said peptide comprises the amino acid sequence of SEQ ID NO:1;
   b) collecting eggs laid by the hens of step a) between seven to twelve weeks after the initial step of injecting;
   c) isolating IgY antibodies from the eggs of step b);
   d) preparing a pharmaceutically acceptable composition comprising the IgY antibodies of step c); and
   e) administering a therapeutically effective amount of the pharmaceutically acceptable composition of step d) to the subject in need thereof by a route of administration selected from the group consisting of intravenous injection, intravenous infusion, intraperitoneal injection, intraperitoneal infusion, intranasal and oral, wherein the therapeutically effective amount is sufficient to inhibit and/or treat said MERS-CoV infection.

13. The method of claim 12, wherein the subject is a camel.

14. The method of claim 12, wherein the subject is a human.

* * * * *

SEQUENCE LISTING

<160> NUMBER OF SEQ ID NOS: 1

<210> SEQ ID NO 1
<211> LENGTH: 1297
<212> TYPE: PRT
<213> ORGANISM: Artificial Sequence
<220> FEATURE:
<223> OTHER INFORMATION: coronaviridae - Middle East Respiratory
      Syndrome Coronavirus Spike Protein, Met1-Trp1297 fragment

<400> SEQUENCE: 1

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
                20                  25                  30

Val Asp Ile Gln Gln Thr Phe Phe Asp Lys Thr Trp Pro Arg Pro Ile
            35                  40                  45

Asp Val Ser Lys Ala Asp Gly Ile Ile Tyr Pro Gln Gly Arg Thr Tyr
        50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270
```

```
Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
                340                 345                 350

Ser Phe Asp Val Glu Ser Gly Val Tyr Ser Val Ser Phe Glu Ala
            355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
            435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
                500                 505                 510

Glu Val Pro Gln Leu Val Asn Ala Asn Gln Tyr Ser Pro Cys Val Ser
    515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
    595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
        675                 680                 685
```

```
Tyr Ser Arg Ser Thr Arg Ser Met Leu Lys Arg Arg Asp Ser Thr Tyr
690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
                835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
                900                 905                 910

Met Gln Gln Gly Pro Ala Ser Ala Arg Asp Leu Ile Cys Ala Gln Tyr
                915                 920                 925

Val Ala Gly Tyr Lys Val Leu Pro Pro Leu Met Asp Val Asn Met Glu
                930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
                980                 985                 990

Asn Gln Lys Leu Ile Ala Asn Lys Phe Asn Gln Ala Leu Gly Ala Met
                995                 1000                1005

Gln Thr Gly Phe Thr Thr Thr Asn Glu Ala Phe Gln Lys Val Gln
   1010             1015                1020

Asp Ala Val Asn Asn Asn Ala Gln Ala Leu Ser Lys Leu Ala Ser
   1025             1030                1035

Glu Leu Ser Asn Thr Phe Gly Ala Ile Ser Ala Ser Ile Gly Asp
   1040             1045                1050

Ile Ile Gln Arg Leu Asp Val Leu Glu Gln Asp Ala Gln Ile Asp
   1055             1060                1065

Arg Leu Ile Asn Gly Arg Leu Thr Thr Leu Asn Ala Phe Val Ala
   1070             1075                1080

Gln Gln Leu Val Arg Ser Glu Ser Ala Ala Leu Ser Ala Gln Leu
   1085             1090                1095

Ala Lys Asp Lys Val Asn Glu Cys Val Lys Ala Gln Ser Lys Arg
```

-continued

```
              1100                1105                1110
Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp
    1295
```